(12) United States Patent
Faden

(10) Patent No.: US 9,907,946 B1
(45) Date of Patent: Mar. 6, 2018

(54) APPARATUS AND METHODS OF DISPENSING FLUID INTRAVENOUSLY AND FLUSHING LINES OF INTRAVENOUS FLUID ADMINISTRATION SYSTEMS

(71) Applicant: Joel S. Faden, Rockville, MD (US)

(72) Inventor: Joel S. Faden, Rockville, MD (US)

(73) Assignee: Joel S. Faden, Rockville, MD (US)

( * ) Notice: Subject to any disclaimer, the term of this patent is extended or adjusted under 35 U.S.C. 154(b) by 0 days.

(21) Appl. No.: 15/405,746

(22) Filed: Jan. 13, 2017

(51) Int. Cl.
*A61M 31/00* (2006.01)
*A61M 39/22* (2006.01)
*A61M 5/168* (2006.01)
*A61M 39/10* (2006.01)
*A61M 39/24* (2006.01)

(52) U.S. Cl.
CPC ...... *A61M 39/225* (2013.01); *A61M 5/16813* (2013.01); *A61M 39/10* (2013.01); *A61M 39/223* (2013.01); *A61M 2039/226* (2013.01); *A61M 2039/229* (2013.01); *A61M 2039/242* (2013.01); *A61M 2039/2406* (2013.01); *A61M 2039/2413* (2013.01)

(58) Field of Classification Search
CPC ................ A61M 39/24; A61M 39/286; A61M 5/16881; A61M 39/225
USPC ......................................................... 604/508
See application file for complete search history.

(56) References Cited

U.S. PATENT DOCUMENTS

| | | | |
|---|---|---|---|
| 2,316,095 A | 4/1943 | Mead, Jr. | |
| 3,982,534 A | 9/1976 | Buckman | |
| 4,447,230 A | 5/1984 | Gula et al. | |
| 4,908,018 A | 3/1990 | Thomsen | |
| 4,946,448 A | 8/1990 | Richmond | |
| 5,807,340 A | 9/1998 | Pokras | |
| 7,931,612 B2 | 4/2011 | Rosenblatt | |
| 2006/0027270 A1 | 2/2006 | Truitt et al. | |
| 2010/0217232 A1* | 8/2010 | Rosenblatt | A61M 5/16881 604/508 |
| 2015/0265827 A1 | 9/2015 | Keyser et al. | |

OTHER PUBLICATIONS

Crosby, E., "Intravenous infusions and one-way valves", Can J Anaesth, Sep. 1991, 38(6), pp. 799.

(Continued)

*Primary Examiner* — Phillip Gray

(74) *Attorney, Agent, or Firm* — Duane Morris LLP

(57) ABSTRACT

Apparatus and methods of dispensing fluid intravenously to a subject, and of flushing a line of an intravenous fluid administration apparatus, are provided. The apparatus may include a chamber including a plurality of connector ports and be configured to operate in fluid communication with an upstream source via a first connector port and, during operation, pass therethrough to downstream tubing, under a first pressure condition, first fluid from the upstream source via a second connector port. A third connector port may be configured to connect to an end of tubing or a valve connector such that, during operation, the chamber is configured to, under a second, higher pressure condition, pass therethrough to the downstream tubing a second fluid from a second fluid source via the third and second connector ports, prevent first fluid flow into the downstream tubing, and prevent second fluid flow through the first connector port.

20 Claims, 29 Drawing Sheets

(56) References Cited

OTHER PUBLICATIONS

Valves Product Information Guide, B. Braun Medical Inc., (2011), 8 pages.
Medline, "Multi-Ad® Fluid Dispensing System by B Braun Medical," accessed Jul. 5, 2017 at http://www.medline.com/product/MULTI-AD-Fluid-Dispensing-System-by-B-Braun-Medical/Accessories/Z05-PF67458#.

* cited by examiner

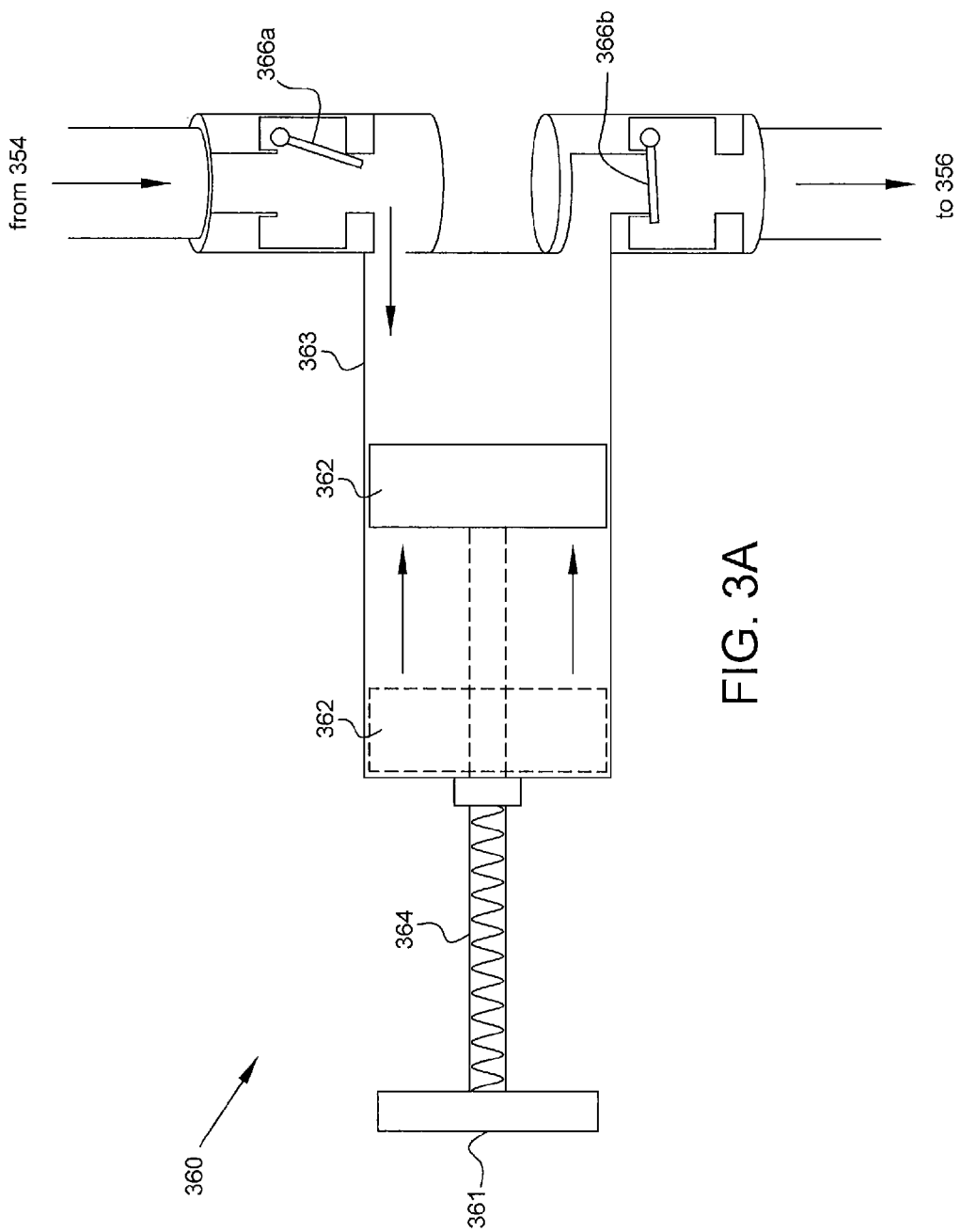

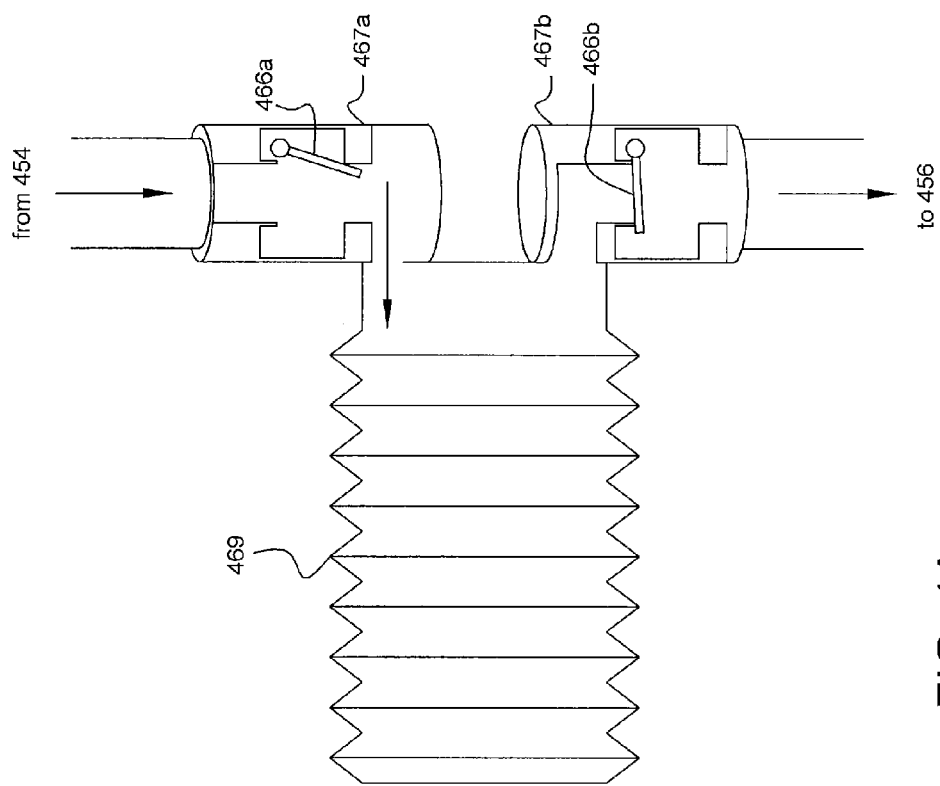

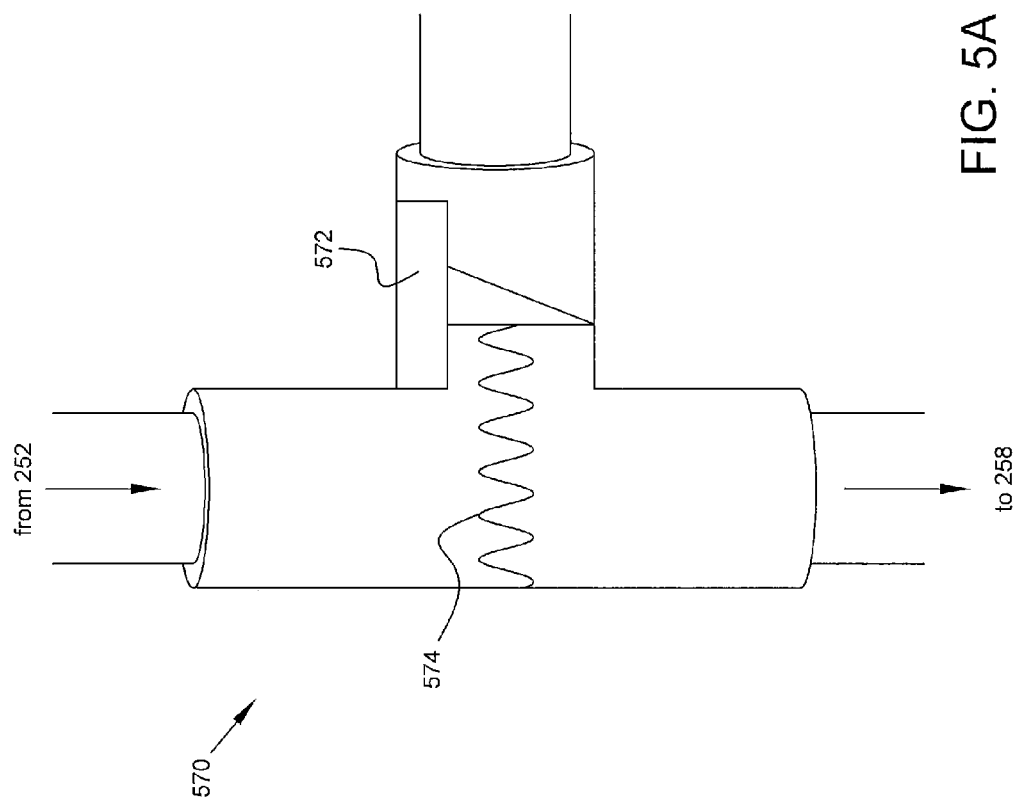

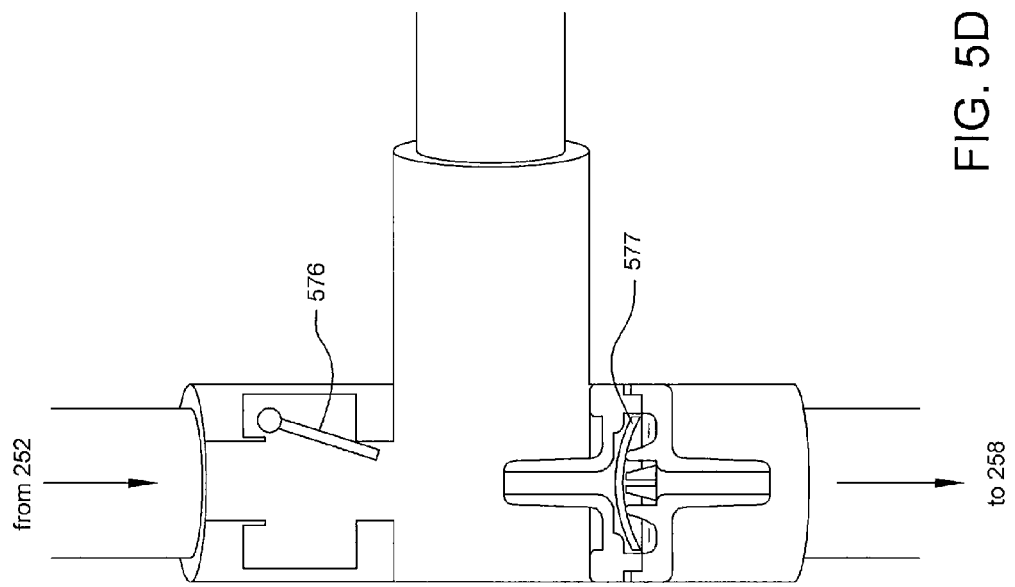

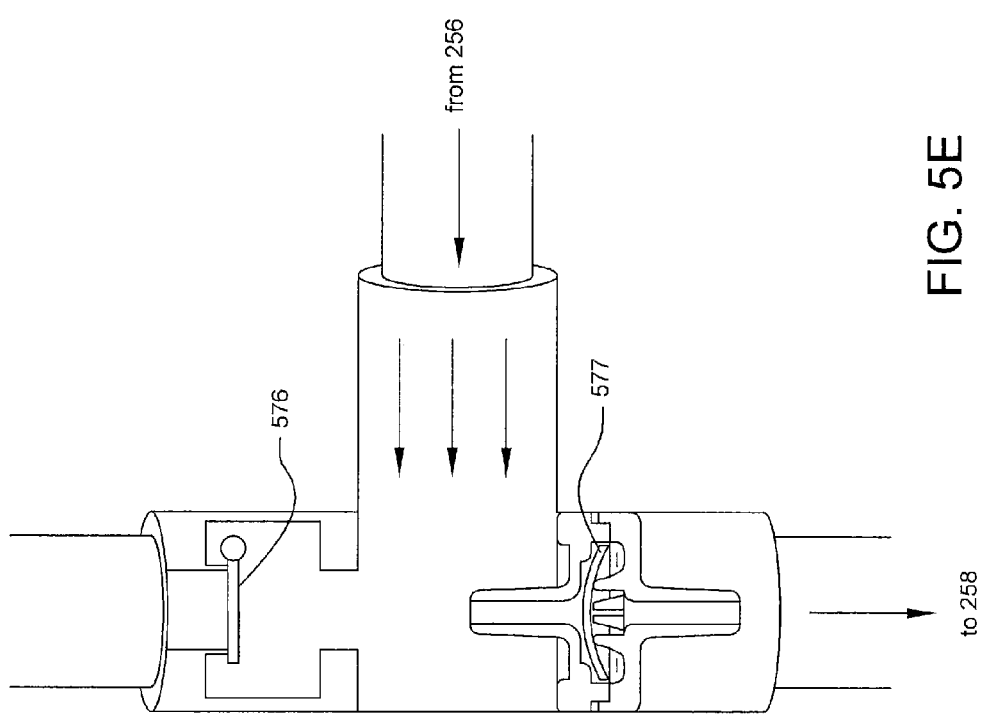

US 9,907,946 B1

APPARATUS AND METHODS OF DISPENSING FLUID INTRAVENOUSLY AND FLUSHING LINES OF INTRAVENOUS FLUID ADMINISTRATION SYSTEMS

FIELD

The present disclosure is directed generally to intravenous fluid administration systems and more particularly to apparatus and methods of dispensing fluid intravenously to a subject, and of flushing a line of an intravenous fluid administration system.

DESCRIPTION OF THE RELATED ART

Conventional intravenous (IV) fluid administration systems include a stopcock (e.g. 3-way stopcock) which is utilized to control the delivery of different IV fluids to a subject (e.g. a human patient). For example, FIG. 1 is a perspective view of a conventional IV fluid administration system. As illustrated in FIG. 1, a conventional IV fluid administration system 100 includes an IV fluid bag 110, a drip chamber 120, a thumb wheel regulator (TWR) 130, a stopcock 140, tubing 152 interconnecting the various components, and a stand 190 which supports and retains the IV bag 110 at an appropriate height above the subject (not shown) to effect the gravity flow of IV fluids to the subject. Typically, the lower end of tubing 152 (not shown) below stopcock 140 is connected to a vascular access device (not shown) (e.g. a needle) that is inserted into a vein of the subject (not shown) to administer IV fluids.

FIG. 1 illustrates a conventional three-way stopcock 140 including a three-way switch 142 and a port 145. In the illustrated configuration (FIG. 1), switch 142 is positioned in an "on to the subject" position such that IV fluid will drain from IV bag 110, through tubing 152, drip chamber 120, TWR 130, and stopcock 140, and into downstream tubing for administration to the subject. In many procedures, a pre-determined amount of a different IV fluid (e.g. drug, antibiotic, anesthetic, etc.) must also be administered to the subject. In such instances, switch 142 is manipulated to an "off to the subject" position (not shown), a syringe (not shown), including a pre-determined amount of the different IV fluid, is inserted into port 145 and is then operated to dispense the different IV fluid into the stopcock 140 and downstream tubing for administration to the subject.

Typically, the stopcock 140 and downstream tubing must be flushed to ensure that all of the predetermined amount of the different IV fluid is administered to the subject. Conventionally, with switch 142 manipulated to an "off to the subject" position (not shown), one or more different syringes (not shown), either respectively pre-filled with flushing IV fluid or flushing IV fluid is drawn into each respective syringe barrel, is respectively inserted into port 145 and operated to flush the stopcock 140 and downstream tubing. If the same port 145 is used for injecting both the different IV fluid (e.g. drug, antibiotic, anesthetic, etc.) and the flushing IV fluid, the port 145 must be sterilized (e.g. with alcohol) before inserting the flushing IV fluid syringe. This process may be repeated numerous times to perform the flush for a single different IV fluid (e.g. drug, antibiotic, anesthetic, etc.), and several different IV fluids may need to be injected, and flushed, while administering IV fluids to a given subject. This process is laborious and time-consuming, and syringes, especially pre-filled syringes, are expensive. The required amount of syringes in this conventional process also contributes to a significant amount of environmental waste.

Another conventional technique for flushing IV lines involves squeezing IV bag 110 (with switch 142 positioned in the "on to the subject" position) to force IV fluid through stopcock 140 and tubing downstream of stopcock 140. However, such a procedure may flood spike and drip chamber 120, rendering it useless, and administers an inaccurate quantity of flushing IV fluid into the subject.

SUMMARY OF THE INVENTION

In some embodiments, an apparatus for dispensing fluid intravenously to a subject is provided that includes a first pressure-operated valve configured to operate in fluid communication with an upstream first source of a first fluid and an upstream reservoir pump configured to automatically refill itself with a second fluid from a second upstream fluid source. The first pressure-operated valve is also configured to, during operation, pass therethrough to tubing downstream of the first pressure-operated valve, under a first pressure condition, the first fluid from the upstream first fluid source. The first pressure-operated valve is also configured to, during operation, pass therethrough to the tubing downstream of the first pressure-operated valve, under a second pressure condition, the second fluid from the upstream reservoir pump, wherein the second pressure condition is a condition of higher pressure than the first pressure condition.

In various embodiments, an apparatus for dispensing fluid intravenously to a subject is provided that includes a reservoir pump configured to operate in fluid communication with an upstream source of a first fluid and a downstream pressure-operated valve. The reservoir pump is also configured to, during operation, automatically refill itself with the first fluid from the first upstream source. The downstream pressure-operated valve is configured to operate in fluid communication with the reservoir pump and a second fluid source upstream of the pressure-operated valve. The downstream pressure-operated valve is also configured to, during operation, dispense the first fluid to tubing downstream of the pressure-operated valve based on a pressure condition within the pressure-operated valve exceeding a threshold pressure.

In various embodiments, a method of flushing a line of an intravenous fluid administration system is provided including introducing a first fluid into tubing configured to transport fluid for intravenous infusion to a subject and operating a reservoir pump upstream of the tubing to dispense a predetermined amount of a second fluid through a pressure-operated valve upstream of the tubing and at a fluid pressure exceeding a threshold pressure of the pressure-operated valve. The method also includes releasing the reservoir pump such that the reservoir pump automatically fills itself with the predetermined amount of the second fluid from a source upstream of the reservoir pump and such that the pressure-operated valve automatically reconfigures itself to receive a third fluid from a fluid source upstream of the pressure-operated valve and at a fluid pressure less than the threshold pressure.

In various embodiments, an apparatus for dispensing fluid intravenously to a subject is provided and includes a chamber comprising a plurality of connector ports. The chamber is configured to operate in fluid communication with an upstream first source of a first fluid via a first one of the plurality of connector ports. The chamber is also configured to, during operation, pass therethrough to tubing downstream of the chamber, under a first pressure condition, the first fluid from the upstream first fluid source via a second one of the plurality of connector ports. A third one of the plurality of connector ports is configured to connect to an end of tubing or a valve connector such that, during operation, the chamber is configured to, under a second pressure condition higher than the first pressure condition, pass therethrough to the tubing downstream of the chamber a second fluid from a second fluid source via the third and second connector ports, prevent flow of the first fluid into the tubing downstream of the chamber, and prevent flow of the second fluid through the first connector port.

In some embodiments, a method of flushing a line of an intravenous fluid administration system is provided including introducing a first fluid into tubing configured to transport fluid for intravenous infusion to a subject via a first connector port and a second connector port of a chamber comprising a plurality of connector ports and at a fluid pressure exceeding a threshold pressure of the chamber. The method also includes introducing a second fluid into the tubing via a third connector port and the second connector port of the chamber and at a fluid pressure exceeding the threshold pressure of the chamber. In each of the introducing steps of the method, the flow of the first fluid or the second fluid through a fourth connector port of the chamber is automatically prevented.

In various embodiments, a method includes operably coupling a first one of a plurality of connector ports of a chamber to an upstream first source of a first fluid such that the chamber is configured to, during operation, pass therethrough to tubing downstream of the chamber, under a first pressure condition, the first fluid via a second one of the plurality of connector ports. The method also includes operably coupling an end of tubing or a valve connector to a third one of the plurality of connector ports of the chamber such that, during operation, the chamber is configured to, under a second pressure condition higher than the first pressure condition pass therethrough to the tubing downstream of the chamber a second fluid from a second fluid source via the third and second connector ports, prevent flow of the first fluid into the tubing downstream of the chamber, and prevent flow of the second fluid through the first connector port.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

FIG. 3A is a plan view of an example of a reservoir pump receiving fluid from an upstream fluid source according to some embodiments.

FIG. 4A is a plan view of an example of a reservoir pump receiving fluid from an upstream fluid source according to some embodiments.

FIG. 5A is a plan view of an example of a pressure-operated valve under a first pressure condition according to some embodiments of the present disclosure.

FIG. 5D is a plan view of an example of a pressure-operated valve under a first pressure condition according to some embodiments of the present disclosure.

FIG. 5E is a plan view of an example of a pressure-operated valve under a second pressure condition according to some embodiments of the present disclosure.

DETAILED DESCRIPTION OF THE EXAMPLES

Figure 1:
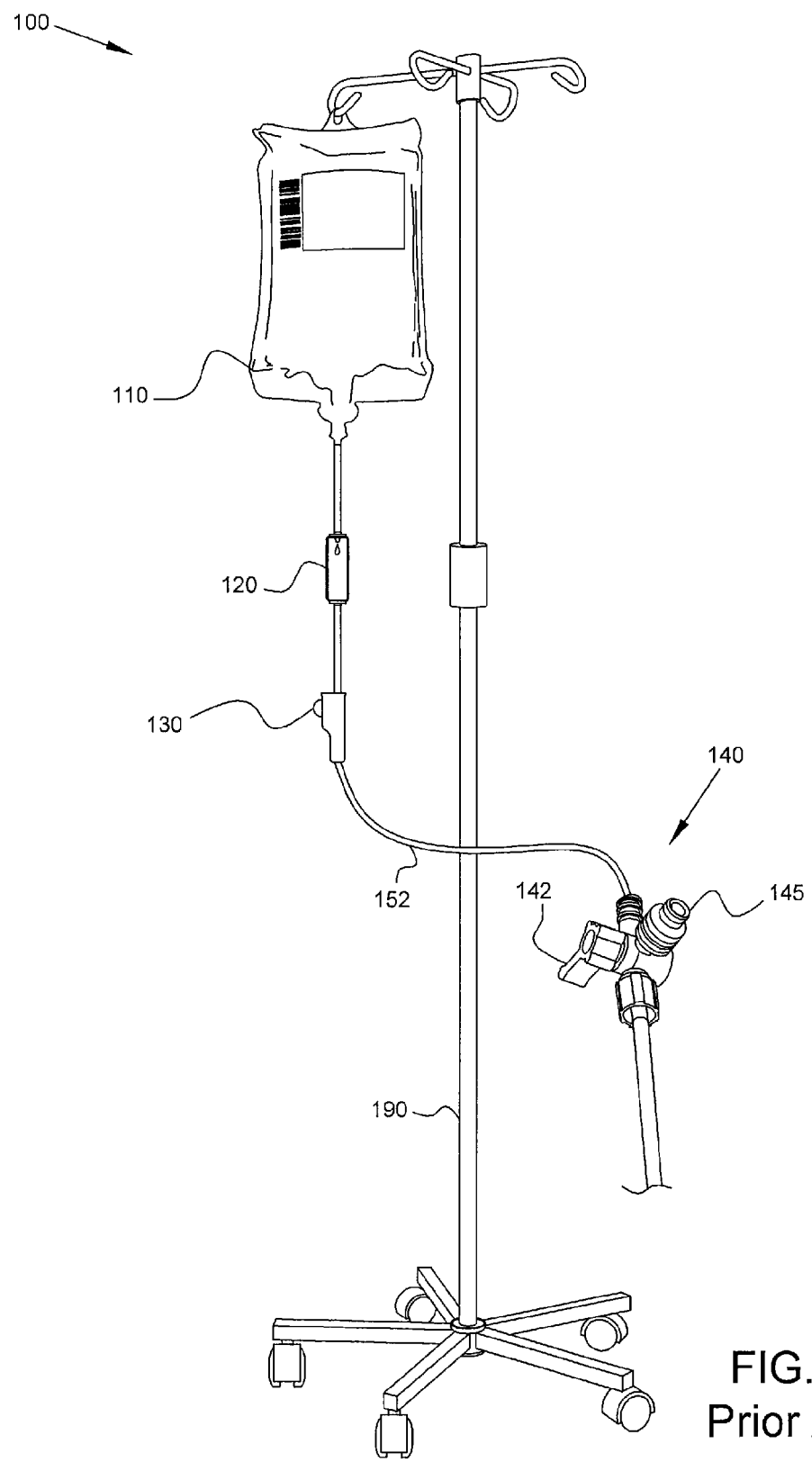
FIG. 1 is a perspective view of a conventional intravenous (IV) fluid administration system.

With reference to the Figures, where like elements have been given like numerical designations to facilitate an understanding of the drawings, the various embodiments of apparatus and methods of dispensing fluid intravenously to a subject, and of flushing a line of an intravenous fluid administration system, are described. The Figures are not drawn to scale.

The following description is provided as an enabling teaching of a representative set of examples. Many changes can be made to the embodiments described herein while still obtaining beneficial results. Some of the desired benefits discussed below can be obtained by selecting some of the features or steps discussed herein without utilizing other features or steps. Accordingly, many modifications and adaptations, as well as subsets of the features and steps described herein are possible and can even be desirable in certain circumstances. Thus, the following description is provided as illustrative and is not limiting.

This description of illustrative embodiments is intended to be read in connection with the accompanying Figures, which are to be considered part of the entire written description. In the description of embodiments disclosed herein, any reference to direction or orientation is merely intended for convenience of description and is not intended in any way to limit the scope of the present disclosure. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise. The term "adjacent" as used herein to describe the relationship between structures/components includes both direct contact between the respective structures/components referenced and the presence of other intervening structures/components between respective structures/components.

As used herein, use of a singular article such as "a," "an" and "the" is not intended to exclude pluralities of the article's object unless the context clearly and unambiguously dictates otherwise.

Improved intravenous fluid administration systems, methods of dispensing fluid intravenously to a subject using such systems, and methods of flushing a line of such systems are provided. The processes described herein are not limited to any specific configuration of an intravenous fluid administration system, nor any specific intravenous fluid. The inventor has developed apparatus and methods of efficiently, cost-effectively, and accurately, dispensing fluid intravenously to a subject, and of efficiently, cost-effectively, and accurately, flushing a line of an intravenous fluid administration system.

The inventor has observed that by utilizing a reservoir pump configured to automatically refill itself with an IV flushing fluid from an upstream IV fluid source and a downstream pressure-operated valve, the time, cost, and environmental waste, necessary for using syringes is minimized. The inventor has also observed that by utilizing a reservoir pump configured to automatically refill itself with an IV flushing fluid from an upstream IV fluid source and a downstream pressure-operated valve, no re-positioning of stopcock switches, and no switching of syringes, is required which results in significant time and cost savings, and provides environmental benefits with the reduction of environmental waste. The inventor has further determined that such solutions are easily scalable such that numerous different IV fluids can be injected and flushed efficiently, cost-effectively, and accurately. The inventor has additionally observed that utilizing a chamber including a plurality of connector ports, where at least the connector port configured to receive fluid from a gravity-fed IV fluid source is automatically operated, the time and cost necessary for using stopcocks is eliminated. These solutions therefore offer significant improvements in the administration of IV fluids to subjects.

Figure 2:
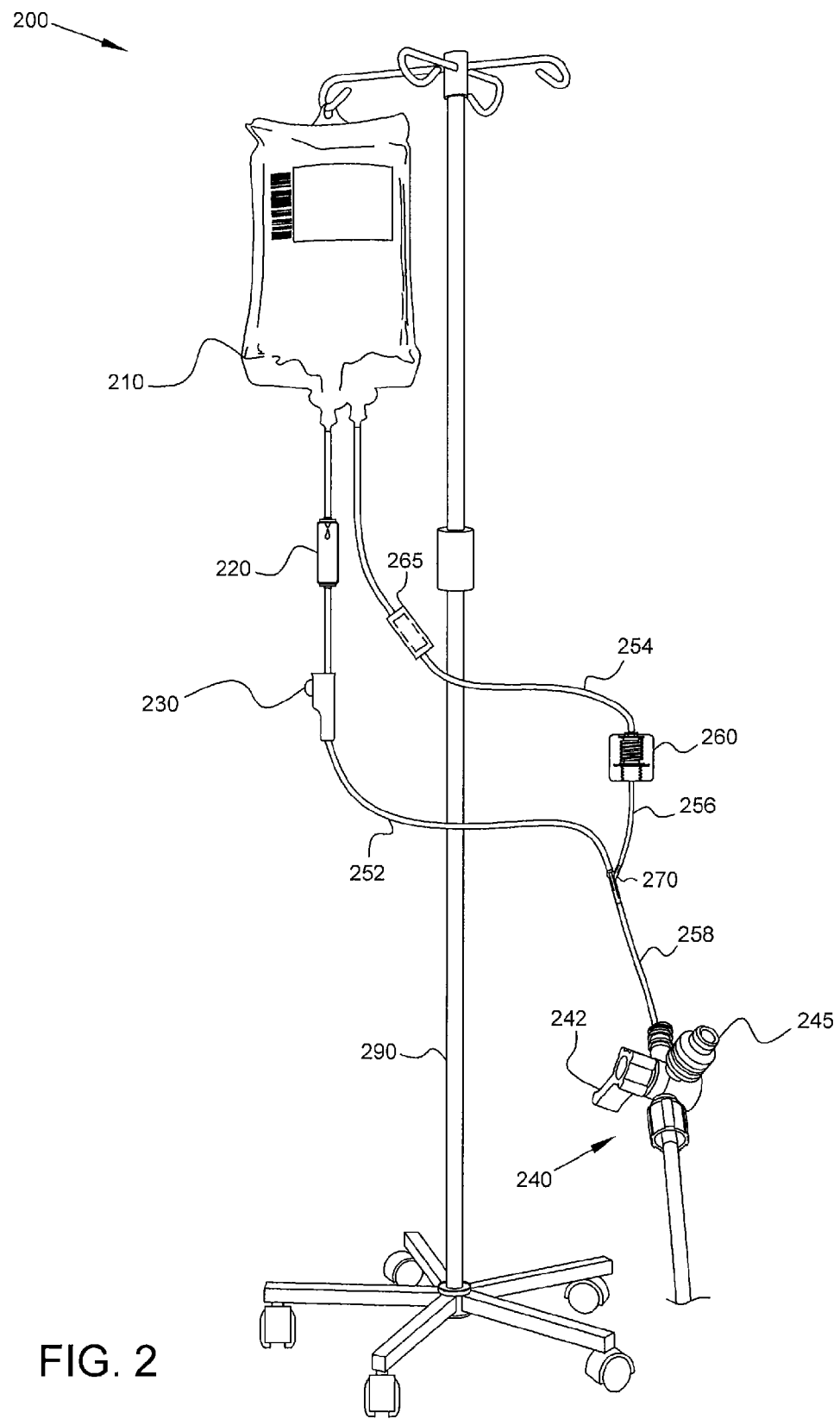
FIG. 2 is a perspective view of an intravenous (IV) fluid administration system according to some embodiments of the present disclosure.

FIG. 2 is a perspective view of an intravenous (IV) fluid administration system 200 according to some embodiments of the present disclosure. As illustrated in FIG. 2, some embodiments include a first source of a first IV fluid such as, for example, an IV fluid bag 210, a plastic IV bottle (not shown), a glass IV bottle (not shown), etc. Any suitable fluid for intravenous administration to a subject may be provided as the first IV fluid. In various embodiments, the first IV fluid is a solution including saline (e.g. 0.9% sodium chloride (NaCl)). In some embodiments, the first IV fluid is a solution including dextrose (e.g. 5% dextrose). In some embodiments, the first IV fluid is a solution including heparin. In some embodiments, the first IV fluid is a solution including one or more additives. For example, a first IV fluid solution may include electrolytes such as, for example, lactated Ringer's solution, and/or vitamins. In some embodiments, the first IV fluid is a solution including saline and dextrose.

As shown in FIG. 2, IV fluid administration system 200 may include a drip chamber 220, a roller clamp such as, for example, thumb wheel regulator (TWR) 230, tubing 252 upstream of drip chamber 220, between drip chamber 220 and TWR 230, and downstream of TWR 230, a stopcock 240, and a stand 290 configured to support and retain the first IV fluid source 210 at an appropriate height above the subject (not shown) to effect the gravity flow of the first IV fluid to the subject. Any suitable tubing may be provided as tubing 252 such as, for example, flexible, plastic tubing. In some embodiments, vented tubing may be utilized. In some embodiments, an air vent (not shown) is included above drip chamber 220. In various embodiments, a spike (not shown) is included above drip chamber 220, and at an upper or proximal end of tubing 252, to initiate the flow of the first IV fluid from the first IV fluid source (e.g. IV fluid bag 210). In various embodiments, stopcock 240 is not included in IV fluid administration system 200.

In various embodiments, a lower or distal end of tubing (not shown) downstream of stopcock 240 is connected to a vascular access device (not shown), such as, for example, a needle (e.g. a butterfly needle), a peripherally inserted central catheter, an over-the-needle catheter, a central venous catheter, a cannula, etc., that is inserted into a vein of the subject (not shown) to administer IV fluids. In various embodiments, the vein is a cephalic, basilica, or median cubital vein in the hand or forearm of a subject. In various embodiments, a male or female adapter (not shown) connects the lower or distal end of tubing (not shown) to a female or male hub of a vascular access device (not shown). In some embodiments, a locking collar can be utilized to further secure the connection between a lower or distal end of tubing (not shown) and hub of a vascular access device (not shown).

In various embodiments, IV fluid administration system 200 includes a pressure-operated valve 270. In various embodiments, pressure-operated valve 270 is configured to operate in fluid communication with first IV fluid source 210, illustrated as upstream from pressure-operated valve 270 via tubing 252, and a reservoir pump 260, also illustrated as upstream from pressure-operated valve 270 via tubing 256. In various embodiments, pressure-operated valve 270 includes male and/or female ends to connect to an end of upstream tubing 252 and an end of downstream tubing 252. In some embodiments, a male and/or female adapter may be utilized to connect pressure-operated valve 270 to an end of upstream tubing 252 and an end of downstream tubing 252.

In various embodiments, reservoir pump 260 is configured to automatically refill itself with a second IV fluid from a second upstream IV fluid source. In various embodiments, reservoir pump 260 includes male and/or female ends to connect to an end of upstream tubing 254 and an end of downstream tubing 252. In some embodiments, a male and/or female adapter may be utilized to connect pressure-operated valve 270 to an end of upstream tubing 252 and an end of downstream tubing 256. As illustrated in FIG. 2, the first and second upstream fluid sources may be the same source (e.g. IV fluid bag 210) and the first and second fluids may be the same type of fluid (e.g. a solution including saline). In various embodiments, the second upstream fluid source may be a different fluid source (not shown) than the first upstream fluid source (e.g. IV fluid bag 210). In various embodiments, the second fluid may be a different type of fluid than the first fluid. For example, the first fluid may be a solution including saline and dextrose, and the second fluid may be a solution including heparin.

In some embodiments, IV fluid administration system 200 includes an observation chamber 265 that is configured to operate in fluid communication with an upstream IV fluid source (e.g. IV fluid bag 210) and reservoir pump 260, and to provide an indication that, during operation, the chamber 265, tubing disposed between the chamber 265 and the reservoir pump 260 (e.g. tubing 254), and the reservoir pump 260, are filled with IV fluid. In various embodiments, observation chamber 265 includes a viewing window or port that permits an operator to observe the level of second IV fluid in chamber 265 and tubing disposed between the chamber 265 and the reservoir pump 260 (e.g. tubing 254). In various embodiments, the viewing window or port is graduated to indicate a precise amount of fluid contained in observation chamber 265, in downstream tubing 254, and in reservoir pump 260.

As illustrated in FIG. 2, reservoir pump 260 is configured to operate in fluid communication with an upstream IV fluid source (e.g. IV fluid bag 210) and a downstream pressure-operated valve 270. In various embodiments, during operation, reservoir pump 260 is configured to dispense IV fluid at a fluid pressure into pressure-operated valve 270 via tubing 256 and to automatically refill itself with IV fluid from the upstream IV fluid source (e.g. IV fluid bag 210). In various embodiments, reservoir pump 260 dispenses a predetermined amount of IV fluid into tubing 256 and pressure-operated valve 270 when operated. Any suitable reservoir pump may be utilized to dispense IV fluid at a fluid pressure into tubing 256 and pressure-operated valve 270.

Referring now to FIG. 3A, a plan view of an example of a reservoir pump receiving fluid from an upstream fluid source according to some embodiments is provided. As shown in FIG. 3A, reservoir pump 360 is connected to tubing 254 and tubing 256. In the illustrated example, reservoir pump 360 includes a plunger assembly including a handle 361 and spring 364 operably coupled to a piston 362 positioned within reservoir pump chamber 363. In various embodiments, reservoir pump chamber 363 is cylindrically-shaped; however, any suitable shape can be utilized for reservoir pump chamber 363. In various embodiments, reservoir pump chamber 363 is formed from a hard plastic material such as, for example, polyethylene, polypropylene, polystyrenes, acrylic polymers, or methacrylic polymers. In some embodiments, reservoir pump chamber 363 is formed from glass. Reservoir pump 360 may include check valves 366a and 366b. In the illustrated example, reservoir pump 360 includes a normally open swing check valve 366a and a normally closed swing check valve 366b. Any suitable check valve may be utilized for check valves 366a and 366b. For example, a swing check valve, lift check valve, wafer check valve, disc check valve, flapper check valve, inline check valve, ball check valve, etc. may be utilized. As shown in FIG. 3A, with piston 362 in its fully retracted position within reservoir pump chamber 363, check valve 366a in a normally opened position, and check valve 366b in a normally closed position, IV fluid from an upstream IV fluid source (e.g. IV fluid bag 210) is received into reservoir pump 360 via tubing 354 until reservoir pump chamber 363 is filled.

Figure 3B:
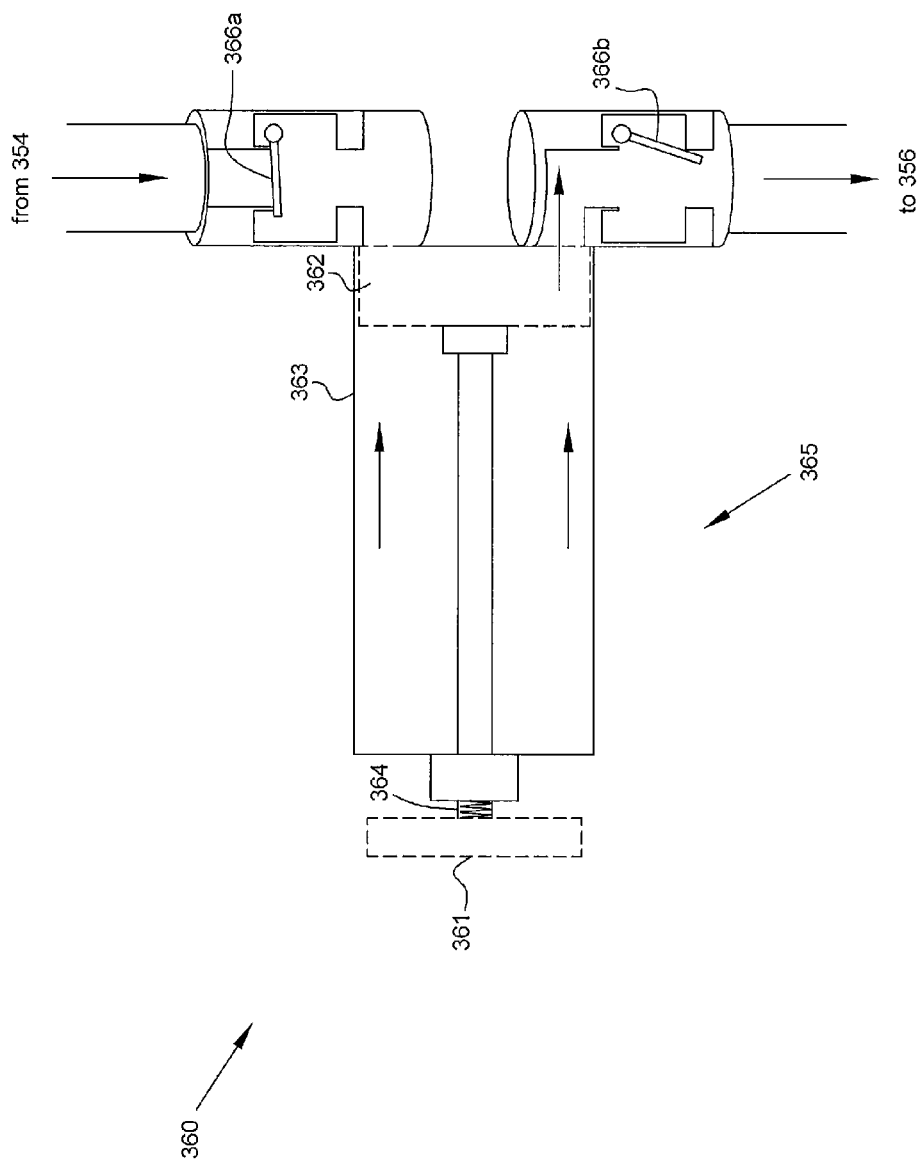
FIG. 3B is a plan view of an example of a reservoir pump dispensing fluid to a downstream fluid sink according to some embodiments.

Referring now to FIG. 3B, a plan view of an example of a reservoir pump dispensing fluid to a downstream fluid sink according to some embodiments is provided. In the illustrated example, during operation, reservoir pump 360 is configured to dispense IV fluid at a fluid pressure into downstream tubing 356. As shown in FIG. 3B, with handle 361 depressed, spring 364 is biased to drive piston 362 into reservoir pump chamber 363 (e.g. laterally) to pressurize the IV fluid in reservoir pump chamber 363. In the illustrated example, the pressurized IV fluid shuts normally opened check valve 366a and opens normally closed check valve 366b to dispense pressurized IV fluid into tubing 356 via check valve 366b. For example, an operator (e.g. a clinician) may grasp reservoir pump 360 and depress handle 361 to initiate a flushing operation. In various embodiments, handle 361 is depressed to fully extend piston 362 through the reservoir pump chamber 363 with a biasing force of spring 364 to fully dispense the IV fluid contained therein into tubing 356 at a fluid pressure. In some embodiments, handle 361 may be depressed to only partially extend piston 364 through the reservoir pump chamber 363 such that only a portion of the IV fluid contained therein is dispensed into tubing 356 at a fluid pressure. In various embodiments, reservoir pump chamber 363 is graduated to identify a precise amount of IV fluid contained therein and/or to provide an indication of the precise amount of fluid dispensed during operation thereof. In various embodiments, when the plunger assembly of reservoir pump 360 is released, spring 364 automatically biases the handle outwardly to carry the piston 362 back through reservoir pump chamber 363 to its fully retracted position (e.g. FIG. 3A), check valve 366a re-opens, and check valve 366b re-shuts. As shown in FIG. 3A, with piston 362 back in its retracted position within reservoir pump chamber 363, check valve 366a back in its normally opened position, and check valve 366b back in its normally closed position, IV fluid from the upstream IV fluid source (e.g. IV fluid bag 210) is received into reservoir pump 360 via tubing 354 until reservoir pump chamber 363 is re-filled.

Figure 3C:
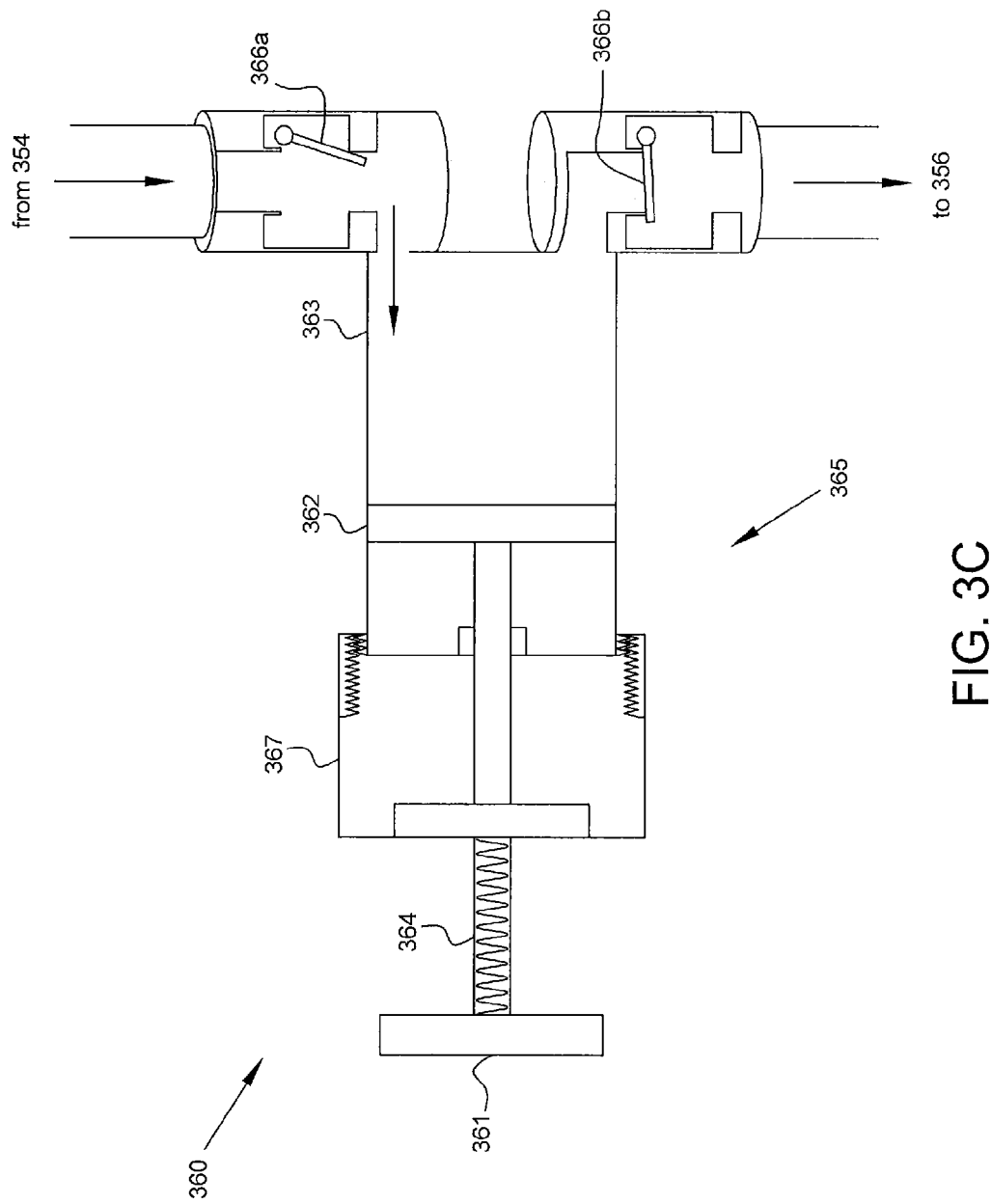
FIG. 3C is a plan view of an example of a reservoir pump including an adjustable filling volume and receiving fluid from an upstream fluid source according to some embodiments.
Figure 3D:
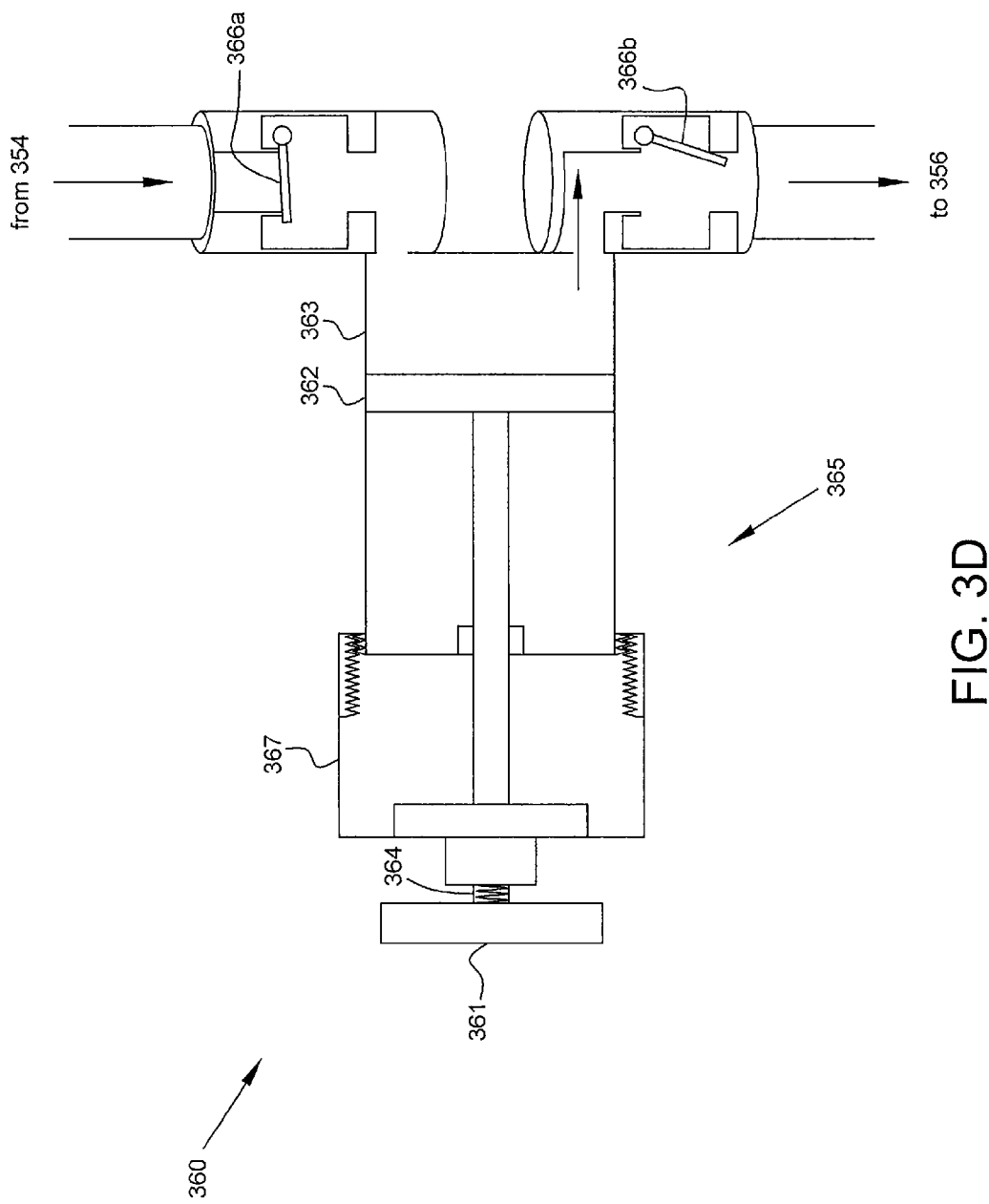
FIG. 3D is a plan view of an example of a reservoir pump including an adjustable filling volume and dispensing fluid to a downstream fluid sink according to some embodiments.
Figure 3E:
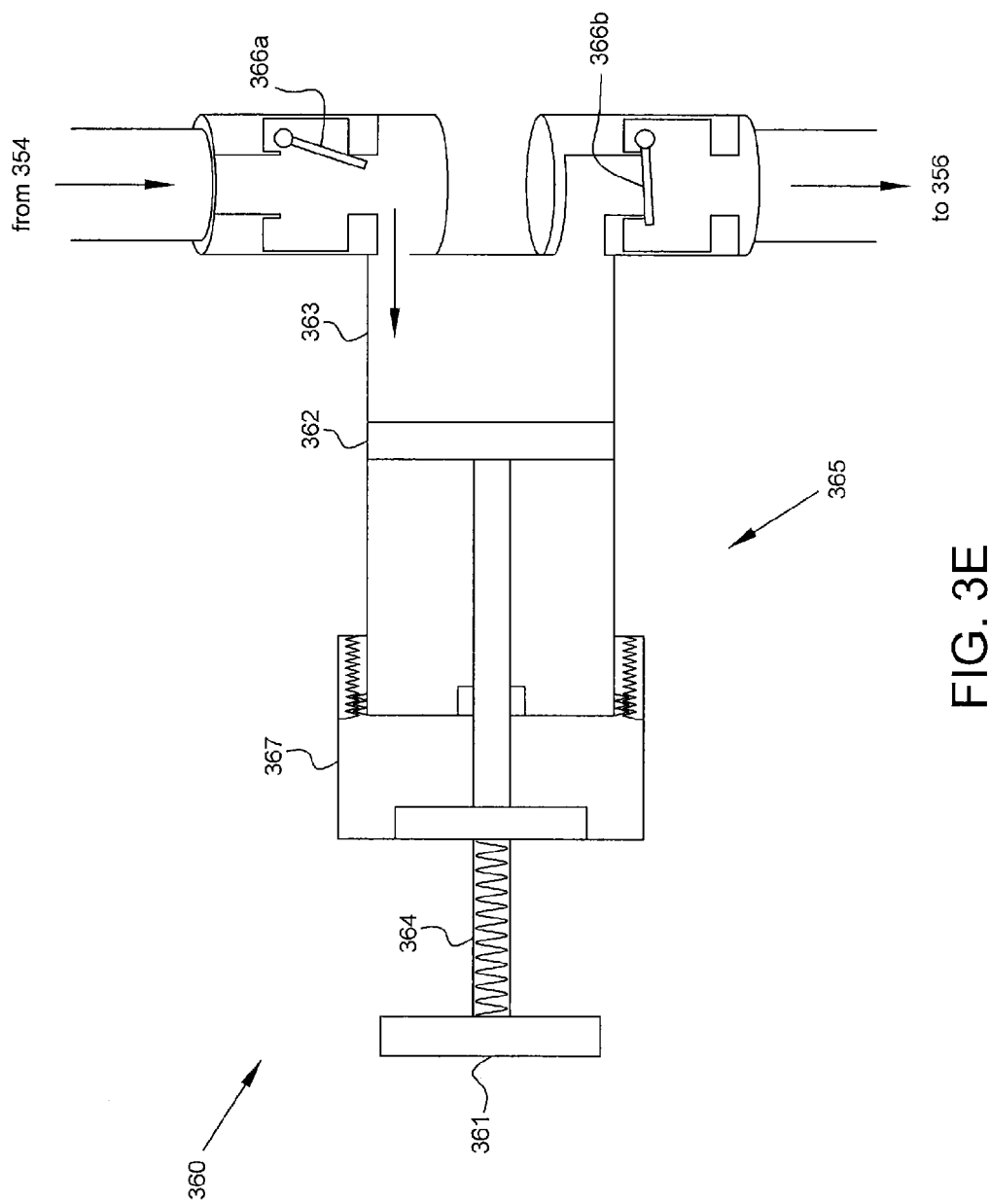
FIG. 3E is a plan view of an example of a reservoir pump including an adjustable filling volume and receiving fluid from an upstream fluid source according to some embodiments.

Referring now to FIGS. 3C and 3E, respective plan views of an example of a reservoir pump including an adjustable filling volume and receiving fluid from an upstream fluid source according to some embodiments is provided. In the illustrated example of FIG. 3C, a portion of reservoir pump chamber 363 is externally threaded to engage with an internally threaded external device 367 (e.g. internally threaded external cylinder, nut, ring, flange, etc.) such that threading of the external device 367 onto reservoir pump chamber 363 adjusts the retracted position of piston 362 within reservoir pump chamber 363 to adjust its filling volume. With reference now to FIG. 3E, in the illustrated example, additional threading of external device 367 onto reservoir pump chamber 363 further adjusts the retracted position of piston 362 within reservoir pump chamber 363 to adjust its filling volume. As shown in the examples of FIGS. 3C and 3E, with piston 362 in its respectively adjusted retracted position within reservoir pump chamber 363, check valve 366a in a normally opened position, and check valve 366b in a normally closed position, IV fluid from an upstream IV fluid source (e.g. IV fluid bag 210) is received into reservoir pump 360 via tubing 354 until the adjusted volume of reservoir pump chamber 363 is filled.

FIG. 3D provides a plan view of an example of a reservoir pump including an adjustable filling volume and dispensing fluid to a downstream fluid sink according to some embodiments. In various embodiments, when the plunger assembly of reservoir pump 360 is released, spring 364 automatically biases the handle 361 outwardly to carry the piston 362 back through reservoir pump chamber 363 to its adjusted retracted position (e.g. FIG. 3C), check valve 366a re-opens, and check valve 366b re-shuts. As shown in FIG. 3C, with piston 362 back in its adjusted retracted position within reservoir pump chamber 363, check valve 366a back in its normally opened position, and check valve 366b back in its normally closed position, IV fluid from the upstream IV fluid source (e.g. IV fluid bag 210) is received into reservoir pump 360 via tubing 354 until the adjusted volume of reservoir pump chamber 363 is re-filled.

Referring now to FIG. 4A, a plan view of an example of a reservoir pump receiving fluid from an upstream fluid source according to some embodiments is provided. In the illustrated example, reservoir pump 460 is connected to tubing 454 and tubing 456, and may include check valves 466a and 466b, as described, for example, in FIGS. 3A-3D. As shown in FIG. 4A, reservoir pump 460 may include a bellows 469. In various embodiments, bellows 469 is elastically deformable. In some embodiments, bellows 469 is formed from a compressible, elastomeric material, such as polyisoprene rubber. In some embodiments, bellows 469 is formed from, for example, low density polyethylene, polypropylene, or a thermoplastic elastomer.

As shown in FIG. 4A, with bellows 469 in its fully released position, check valve 466a in a normally opened position, and check valve 466b in a normally closed position, IV fluid from an upstream IV fluid source (e.g. IV fluid bag 210) is received into bellows 469 via tubing 454 until bellows 469 is filled. During operation, bellows 469 may be compressed to shut normally opened check valve 466a, open normally closed check valve 466b, and dispense pressurized IV fluid into tubing 456 via check valve 466b. For example, an operator (e.g. a clinician) may grasp and compress bellows 469 to initiate a flushing operation. In various embodiments, when bellows 469 is released, it will automatically expand and return to its decompressed form which re-opens check valve 466a, and re-shuts check valve 466b. As shown in FIG. 4A, with bellows 469 returned to its decompressed form, check valve 466a back in its normally opened position, and check valve 466b back in its normally closed position, IV fluid from the upstream IV fluid source (e.g. IV fluid bag 210) is received into bellows 469 via tubing 454 until bellows 469 is re-filled.

Figure 4B:
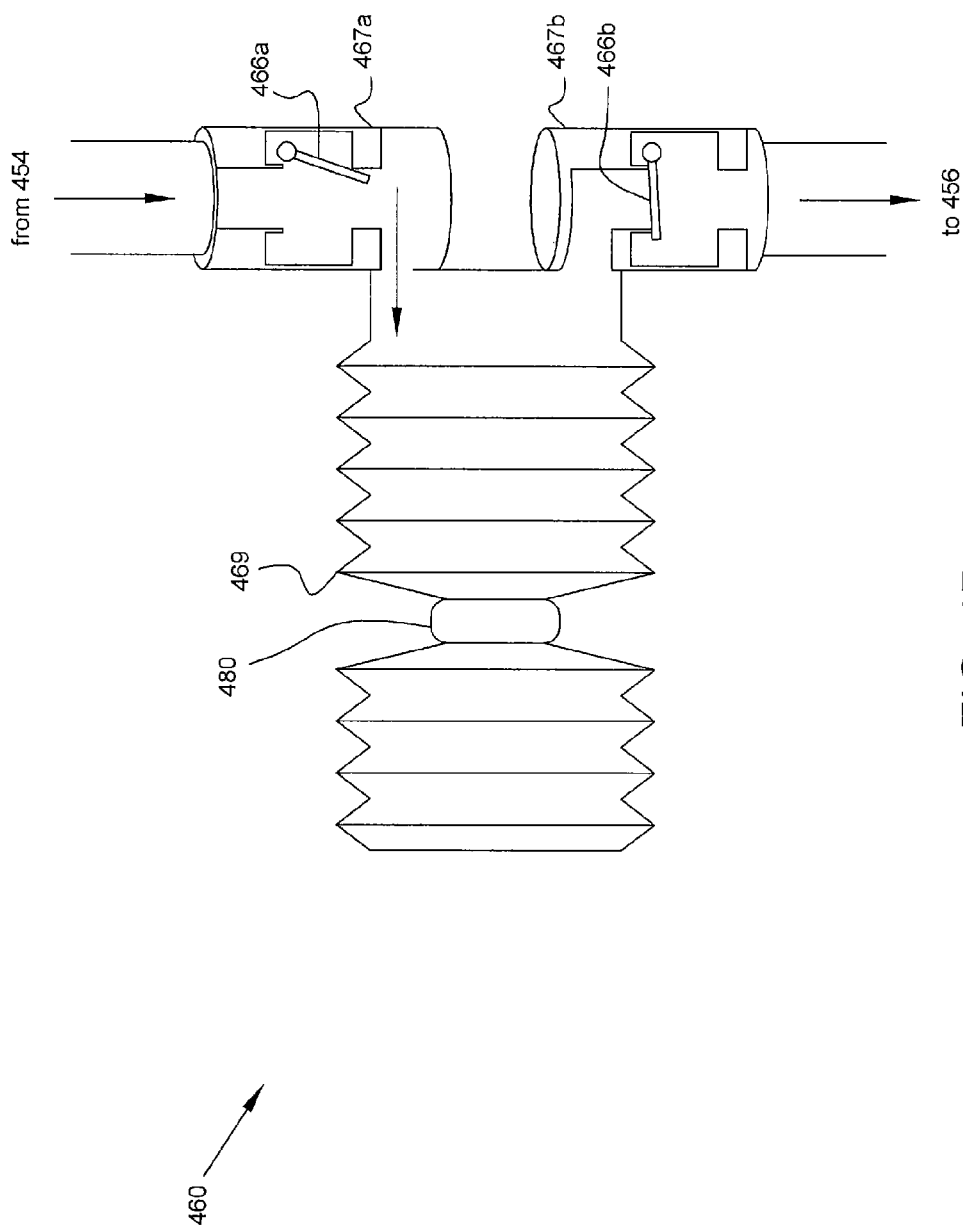
FIG. 4B is a plan view of an example of a reservoir pump including an adjustable filling volume and receiving fluid from an upstream fluid source according to some embodiments.

Referring now to FIG. 4B, a plan view of an example of a reservoir pump including an adjustable filling volume and receiving fluid from an upstream fluid source according to some embodiments is provided. In the illustrated example, a compression device 480 (e.g. clamp, ring, flange, locking collar, etc.) restricts the fillable volume of bellows 469 to the volume forward of the compression device. As shown in FIG. 4B, with compression device 460 installed surrounding a portion of bellows 469, check valve 466a in a normally opened position, and check valve 466b in a normally closed position, IV fluid from an upstream IV fluid source (e.g. IV fluid bag 210) is received into reservoir pump 460 via tubing 454 until bellows 469 is filled.

As described above for FIG. 4A, during operation, the filled portion of bellows 469 may be compressed to shut normally opened check valve 466a, open normally closed check valve 466b, and dispense pressurized IV fluid from the adjusted filling volume of bellows 469 into tubing 456 via check valve 466b. In various embodiments, when this portion of bellows 469 is released, it will automatically expand and return to its decompressed form which re-opens check valve 466a, and re-shuts check valve 466b. As shown in FIG. 4A, with the filling portion of bellows 469 returned to its decompressed form, check valve 466a back in its normally opened position, and check valve 466b back in its normally closed position, IV fluid from the upstream IV fluid source (e.g. IV fluid bag 210) is received into the filling portion of bellows 469 via tubing 454 until this portion of bellows 469 is re-filled.

Referring again to FIG. 2, in various embodiments, pressure-operated valve 270 is configured to, during operation, pass therethrough to tubing downstream (e.g. tubing 258) of the pressure-operated valve 270, under a first pressure condition, the first IV fluid from the upstream first fluid source (e.g. IV fluid bag 210), and, during operation, pass therethrough to the tubing downstream (e.g. tubing 258) of the pressure-operated valve 270, under a second pressure condition, the second IV fluid from the upstream reservoir pump 260, where the second pressure condition is a condition of higher pressure than the first pressure condition. For example, the first pressure may be the fluid pressure of gravity-fed first IV fluid entering pressure-operated valve 270 via tubing 252, and the second pressure may be the fluid pressure of pressurized second IV fluid from reservoir pump 260 entering pressure-operated valve 270 via tubing 256. Any suitable pressure-operated valve 270 may be utilized to selectively dispense either the first IV fluid (e.g. gravity-fed from IV fluid bag 210 via tubing 252) or the second IV fluid (e.g. from reservoir pump 260 via tubing 256) to downstream tubing 258 based on a pressure condition within pressure-operated valve 270. In various embodiments, pressure-operated valve 270 is set at a threshold pressure such that, when such threshold pressure is met and/or exceeded, second IV fluid (e.g. dispensed from reservoir pump 260 via tubing 256), rather than first IV fluid (e.g. gravity-fed from IV fluid bag 210 via tubing 252), is passed therethrough and dispensed to downstream tubing 258.

Referring now to FIG. 5A, a plan view of an example of a pressure-operated valve under a first pressure condition according to some embodiments is provided. As shown in FIG. 5A, pressure-operated valve 570 is connected to tubing 252, tubing 258, and tubing 256. In the illustrated example, pressure-operated valve 570 includes a spring 574 operably coupled to a piston 572. As shown in FIG. 5A, piston 574 may be generally "T" shaped in cross section including a longitudinal rod portion that is operably coupled to spring 574 and a transversal rod portion disposed above the same. Any suitable shape may be provided for piston 572 and spring 574. In various embodiments, spring 574 is biased at a pre-determined threshold pressure for pressure-operated valve 570. As illustrated in FIG. 5A, during normal operation, second IV fluid pressure from reservoir pump 260 and via tubing 256 is minimal; thus, spring 574 is biased to extend piston 572 toward tubing 256 and first IV fluid gravity-fed from upstream first IV fluid source (e.g. IV fluid bag 210) via tubing 252 is passed through pressure-operated valve 570 and into downstream tubing 258.

Figure 5B:
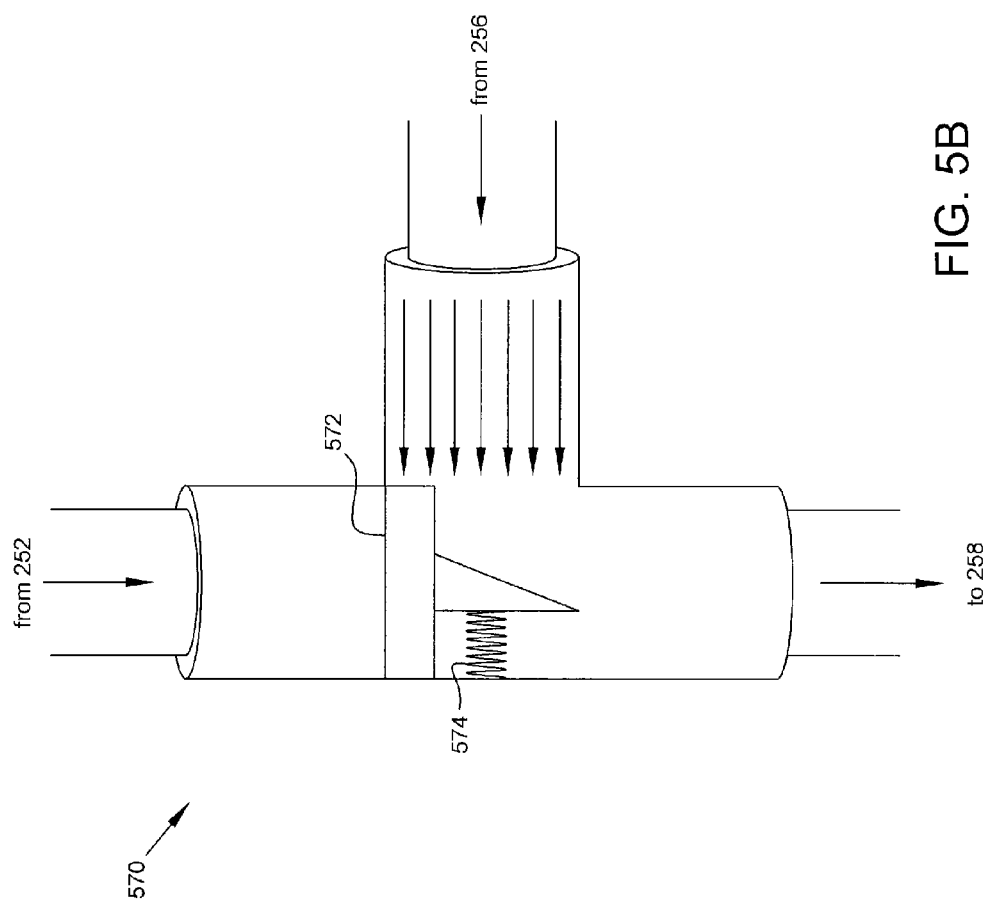
FIG. 5B is a plan view of an example of a pressure-operated valve under a second pressure condition according to some embodiments of the present disclosure.

Referring now to FIG. 5B, a plan view of an example of a pressure-operated valve under a second pressure condition according to some embodiments is provided. In various embodiments, during a reservoir pump-use operation (e.g. a flushing operation), pressurized second IV fluid is received from reservoir pump 260 and into pressure-operated valve 570 via tubing 256. As illustrated in FIG. 5B, the pressurized second IV fluid applies a fluid pressure to piston 572. In the illustrated example, when the fluid pressure received from reservoir pump 260 via tubing 256 is at or exceeds a threshold biasing pressure of spring 574, piston 572 compresses spring 574 to reposition the transversal rod portion of piston 572 to block fluid flow from tubing 252 and provide fluid communication between the inlet from tubing 256 and the outlet to tubing 258. When the fluid pressure received from reservoir pump 260 via tubing 256 is again less than the threshold biasing pressure of spring 574, spring 574 biases piston 572 back toward tubing 256 to re-open the inlet from tubing 252, provide fluid communication between the inlet from tubing 252 and the outlet to tubing 258, and block fluid flow from tubing 256.

Figure 5C:
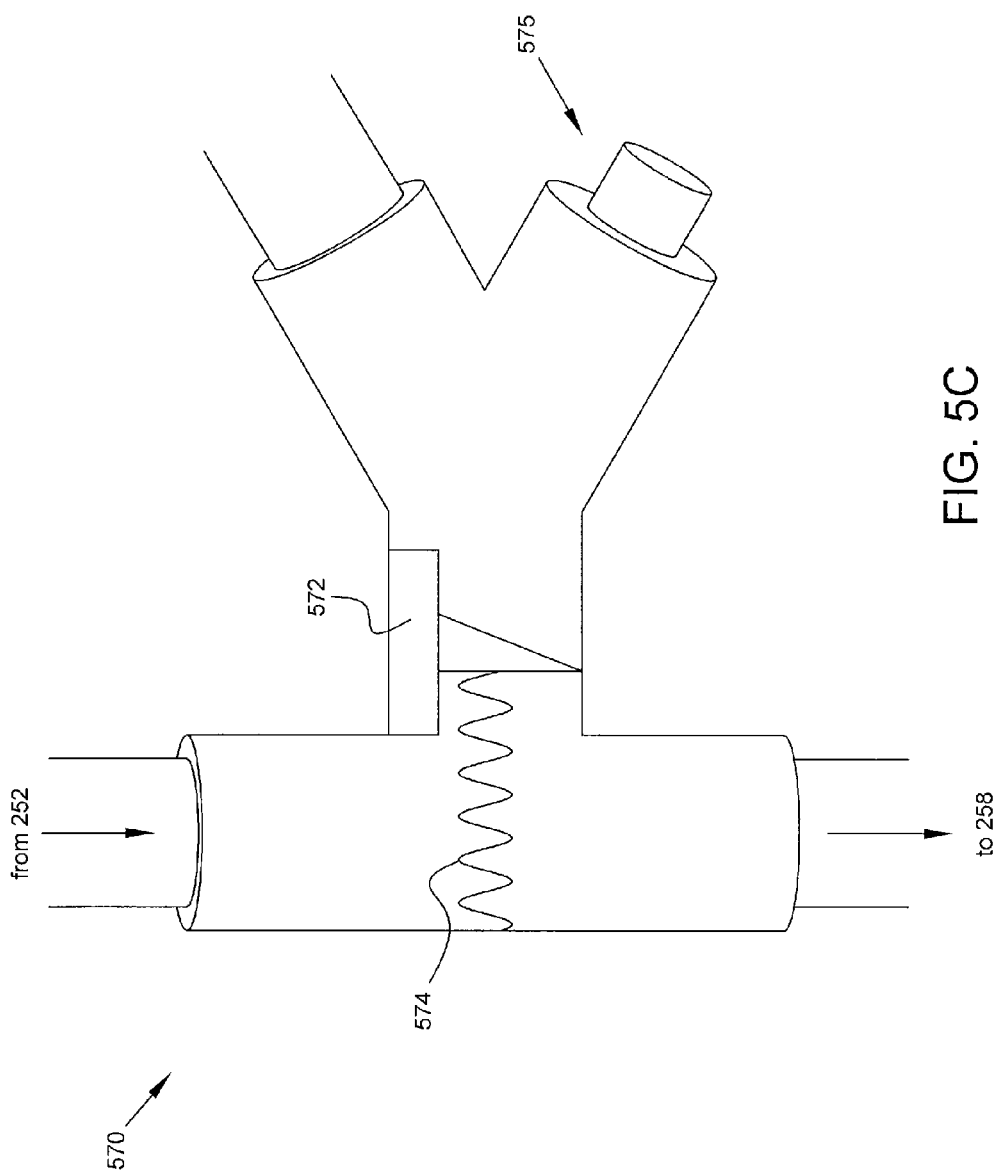
FIG. 5C is a plan view of an example of a pressure-operated valve under a first pressure condition according to some embodiments of the present disclosure.

FIG. 5C is a plan view of an example of a pressure-operated valve under a first pressure condition according to some embodiments of the present disclosure. In the illustrated example, pressure-operated valve 570 is connected to tubing 252, tubing 258, and tubing 256, and includes a spring 574 operably coupled to a piston 572 as described above for FIGS. 5A-5B. As illustrated in FIG. 5C, pressure-operated valve 570 may include a port connector 575 such as, for example, a luer lock connector. In various embodiments, pressure-operated valve 570 may include a male or female connector end to connect to an end of a port connector 575. In various embodiments, port connector 575 may be integral to pressure-operated valve 570. In various embodiments, a female end of port connector 575 (e.g. luer lock connector) serves as a connection point through which a third IV fluid (e.g. drug, antibiotic, anesthetic, etc.) is introduced at a fluid pressure into pressure-operated valve 570 (e.g. via a syringe (not shown)).

The pressurized third IV fluid may apply a fluid pressure to piston 572 and, as described above for FIG. 5B and the second IV fluid from reservoir pump 260 via tubing 256, when the fluid pressure received via port connector 575 is at or exceeds a threshold biasing pressure of spring 574, piston 572 compresses spring 574 to reposition the transversal rod portion of piston 572 to block fluid flow from tubing 252 and provide fluid communication between the port connector 575 and the outlet to tubing 258. When the fluid pressure received via port connector 575 is again less than the threshold biasing pressure of spring 574, spring 574 biases piston 572 back toward tubing 256 to re-open the inlet from tubing 252, provide fluid communication between the inlet from tubing 252 and the outlet to tubing 258, and block fluid flow from port connector 575 and tubing 256. In various embodiments, port connector 575 includes a filter (not shown). In some embodiments port connector 575 includes a normally closed check valve (not shown). In various embodiments, subsequent to injecting a third IV fluid into pressure-operated valve 570 via port connector 575 (e.g. luer lock connector), a flushing operation using reservoir pump 260 can be initiated as described above for FIGS. 2, 3A-4B, and 5B.

FIG. 5D is a plan view of an example of a pressure-operated valve under a first pressure condition according to some embodiments of the present disclosure. As shown in FIG. 5D, pressure-operated valve 570 is connected to tubing 252, tubing 258, and tubing 256. In various embodiments, pressure-operated valve 570 includes one or more check valves. In various embodiments, pressure-operated valve 570 may include a check valve positioned within the valve inlet from tubing 252. As shown in FIG. 5D, pressure-operated valve 570 may include a check valve positioned within the valve inlet from tubing 252 and a check valve within the valve outlet to tubing 258. In the illustrated example, pressure-operated valve 570 includes a normally open swing check valve 576 within the valve inlet from tubing 252 and a normally open disc check valve 577 within the valve outlet to tubing 258. Any suitable check valve may be utilized as check valve 576 and check valve 577. As illustrated in FIG. 5D, during normal operation, second IV fluid pressure from reservoir pump 260 and via tubing 256 is minimal; thus, first IV fluid gravity-fed from upstream first IV fluid source (e.g. IV fluid bag 210) via tubing 252 is passed through pressure-operated valve 570 and into downstream tubing 258. In various embodiments, pressure-operated valve 570 includes a check valve (not shown) positioned within the valve inlet from tubing 256. In various embodiments, fluid pressure from below check valve 577 (e.g. back flow from tubing 258) will operate the disc to shut check valve 577 and prevent any flow of fluid from tubing 258 from entering pressure-operated valve 570.

Referring now to FIG. 5E, a plan view of an example of a pressure-operated valve under a second pressure condition according to some embodiments is provided. In various embodiments, during a reservoir pump-use operation (e.g. a flushing operation), pressurized second IV fluid is received from reservoir pump 260 and into pressure-operated valve 570 via tubing 256. As illustrated in FIG. 5B, the pressurized second IV fluid applies a fluid pressure to shut check valve 576. In the illustrated example, when the fluid pressure received from reservoir pump 260 via tubing 256 is at or exceeds a threshold pressure of check valve 576, check valve 576 shuts to block fluid flow from tubing 252 and provide fluid communication between the inlet from tubing 256 and the outlet to tubing 258 via check valve 577. When the fluid pressure received from reservoir pump 260 via tubing 256 is again less than the threshold pressure of check valve 576, check valve 576 re-opens to re-open the inlet from tubing 252, and provide fluid communication between the inlet from tubing 252 and the outlet to tubing 258 via check valve 577.

Figure 5F:
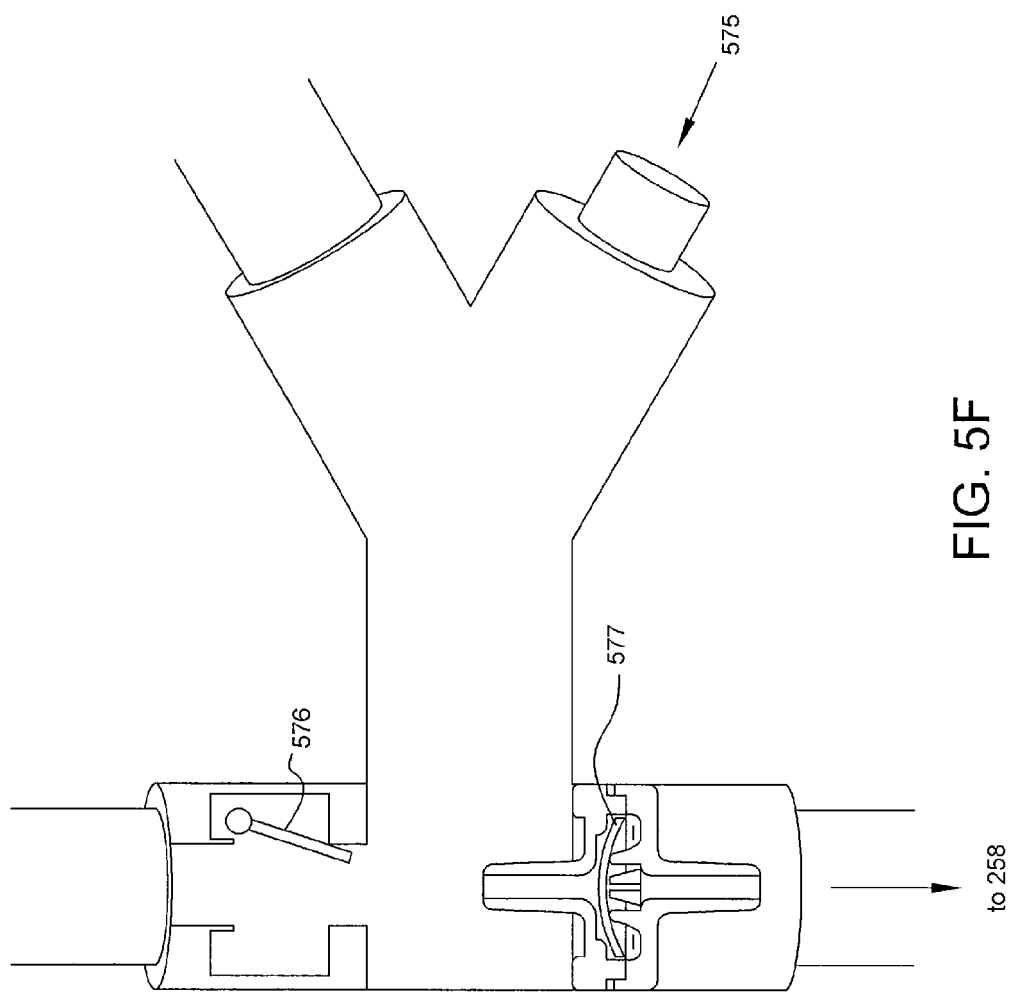
FIG. 5F is a plan view of an example of a pressure-operated valve under a first pressure condition according to some embodiments of the present disclosure.

FIG. 5F is a plan view of an example of a pressure-operated valve under a first pressure condition according to some embodiments. In the illustrated example, pressure-operated valve 570 is connected to tubing 252, tubing 258, and tubing 256, and includes check valves 576 and 577 as described above for FIGS. 5E-5F. As illustrated in FIG. 5F, pressure-operated valve 570 may include a port connector 575 (e.g. luer lock connector) as described above for FIG. 5C. In various embodiments, pressurized third IV fluid injected via port connector 575 (e.g. luer lock connector) may apply a fluid pressure to check valve 576 and, as described above for FIG. 5E and the second IV fluid from reservoir pump 260 via tubing 256, when the fluid pressure received via port connector 575 is at or exceeds a threshold pressure of check valve 576, check valve 576 shuts to block fluid flow from tubing 252 and provide fluid communication between the inlet from tubing 256 and the outlet to tubing 258 via check valve 577. When the fluid pressure received via port connector 575 is again less than the threshold pressure of check valve 576, check valve 576 re-opens to re-open the inlet from tubing 252, and provide fluid communication between the inlet from tubing 252 and the outlet to tubing 258 via check valve 577. In various embodiments, port connector 575 includes a filter (not shown). In some embodiments, port connector 575 includes a normally closed check valve (not shown). In various embodiments, subsequent to injecting a third IV fluid into pressure-operated valve 570 via port connector 575 (e.g. luer lock connector), a flushing operation using reservoir pump 260 can be initiated as described above for FIGS. 2, 3A-4B, and 5E.

Figure 6:
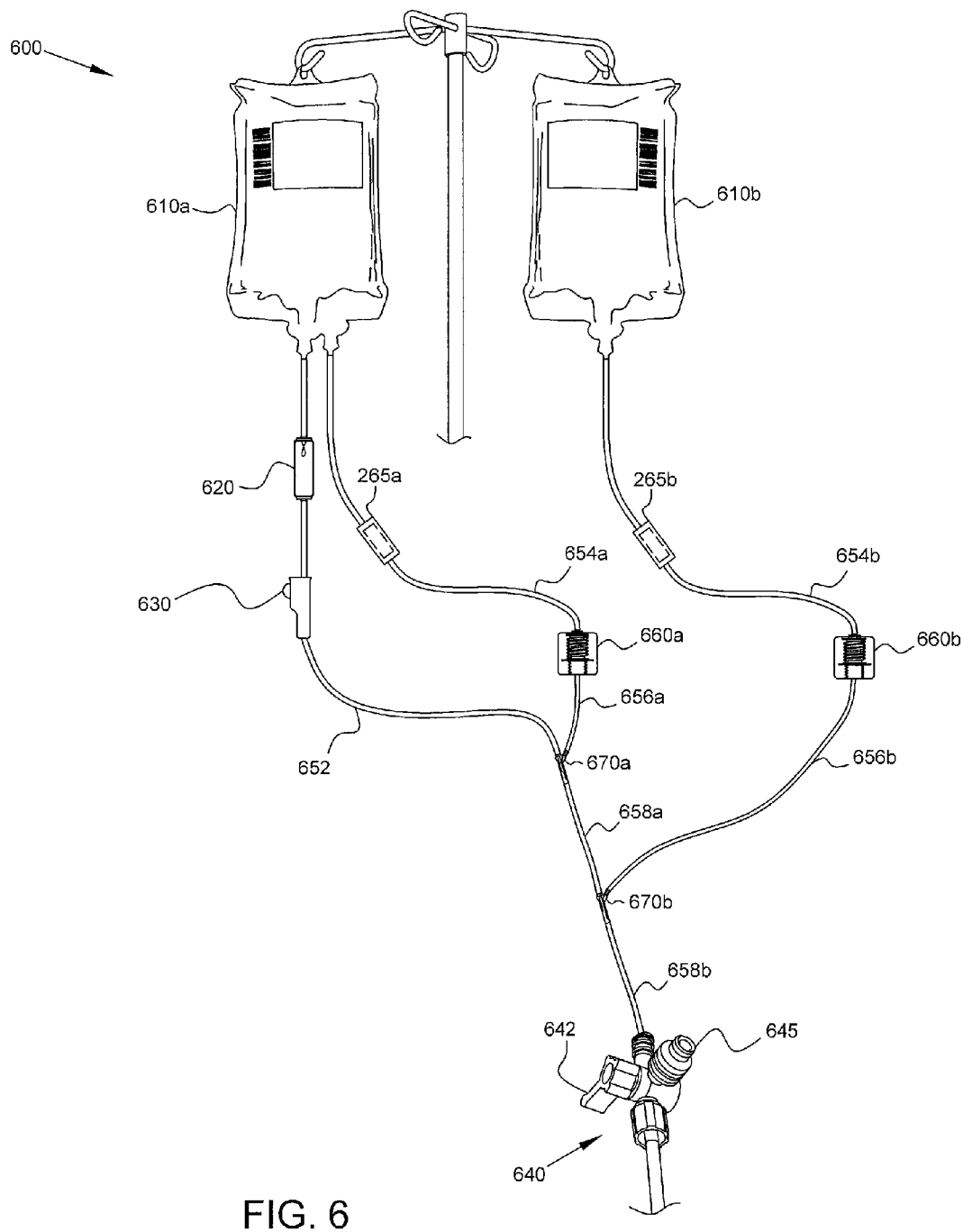
FIG. 6 is a perspective view of an intravenous (IV) fluid administration system according to some embodiments of the present disclosure.

With reference to FIG. 6, a perspective view of an intravenous (IV) fluid administration system according to some embodiments is provided. As illustrated in FIG. 6, some embodiments include a first source of a first IV fluid 610a, a drip chamber 620, a roller clamp 630, tubing 652 upstream of drip chamber 620, between drip chamber 620 and roller clamp 630, and downstream of roller clamp 630, a stopcock 640, and a stand 690 as described above for FIG. 2. In various embodiments, stopcock 640 is not included in IV fluid administration system 600. In various embodiments, IV fluid administration system 600 includes a first pressure operated valve 670a as described above for pressure operated valve 270 (570) for FIGS. 2, 5A-5F. In various embodiments, IV fluid administration system 600 includes a first reservoir pump 660a, and tubing 656a between first reservoir pump 660a and first pressure operated valve 670a, as described above for reservoir pump 260 (360, 360) for FIGS. 2, 3A-4B and pressure operated valve 270 (570) for FIGS. 2, 5A-5F. In various embodiments, IV fluid administration system 600 includes a first observation chamber 665a, and tubing 654a between first reservoir pump 660a and first observation chamber 665a, as described above for observation chamber 265 and reservoir pump 260 (360, 360) for FIGS. 2, 3A-4B. In various embodiments, first IV fluid source 610a and the IV fluid source of first reservoir pump 660a (not shown) are different IV fluid sources as described above for FIG. 2. In the illustrated embodiments, first IV fluid source 610a and the IV fluid source of first reservoir pump 660a are the same IV fluid source (610a).

The inventor has determined that his solutions described herein are easily scalable such that numerous different IV fluids can be injected and flushed efficiently, cost-effectively, and accurately. For example, as shown in FIG. 6, IV fluid administration system 600 may include an another upstream IV fluid source 610b and another upstream reservoir pump 660b configured to automatically refill itself with a third IV fluid from the another upstream IV fluid source 610b as described above for reservoir pump 260 (360, 460) for FIGS. 2, 3A-4B. In the illustrated embodiments, first IV fluid source 610a and the IV fluid source 610b of second reservoir pump 660b are different IV fluid sources. In various embodiments, first IV fluid source 610a and the IV fluid source 610b of second reservoir pump 660b are the same IV fluid source (not shown). In some embodiments, IV fluid administration system 600 includes a second observation chamber 665b that is configured to operate in fluid communication with the another upstream IV fluid source 610b and the another upstream reservoir pump 660b, and to provide an indication that, during operation, the second chamber 665b, tubing disposed between the chamber 665b and the another upstream reservoir pump 660b (e.g. tubing 654b), and the another upstream reservoir pump 660b, are filled with IV fluid, as described above for observation chamber 265 and reservoir pump 260 (360, 360) for FIGS. 2, 3A-4B.

As illustrated in FIG. 6, the another upstream reservoir pump 660b is configured to operate in fluid communication with the another upstream IV fluid source 610b and a downstream second pressure-operated valve 670b as described above for reservoir pump 260 (360, 360) for FIGS. 2, 3A-4B and pressure operated valve 270 (570) for FIGS. 2, 5A-5F. In various embodiments, during operation, the another upstream reservoir pump 660b is configured to dispense IV fluid at a fluid pressure into second pressure-operated valve 670b via tubing 656b and to automatically refill itself with IV fluid from the another upstream IV fluid source 610b as described above for reservoir pump 260 (360, 360) for FIGS. 2, 3A-4B and pressure operated valve 270 (570) for FIGS. 2, 5A-5F. In various embodiments, the another upstream reservoir pump 660b dispenses a predetermined amount of IV fluid into tubing 656b and second pressure-operated valve 670b when operated. Any suitable reservoir pump may be utilized to dispense IV fluid at a fluid pressure into 656b and second pressure-operated valve 670b.

In the illustrated embodiments, IV fluid administration system 600 may include a second pressure-operated valve 670b that is configured to operate in fluid communication with the upstream first IV fluid source 610a (as described above for pressure-operated valve 270 (570) for FIGS. 2, 5A-5F) or the upstream reservoir pump 660a depending on which fluid is passing through upstream tubing 658a. In various embodiments, second pressure-operated valve 670b is also configured to operate in fluid communication with another upstream reservoir pump 660b (as described above for reservoir pump 260 (360, 360) for FIGS. 2, 3A-4B and pressure operated valve 270 (570) for FIGS. 2, 5A-5F) that is configured to automatically refill itself with a third IV fluid from the another upstream IV fluid source 610b. In various embodiments, neither the IV fluid source of first reservoir pump 660a (not shown) nor the IV fluid source of second reservoir pump 660b (610b) are the same IV fluid source as first IV fluid source 610a. In various embodiments, first IV fluid source 610a and the IV fluid source of first reservoir pump 660a are the same IV fluid source (610a) and the IV fluid source of second reservoir pump 660b (610b) is a different IV fluid source.

In various embodiments, during operation, second pressure-operated valve 670b is configured to pass therethrough to tubing 658b downstream of the second pressure-operated valve 670b, under a third pressure condition, the first fluid from the upstream first IV fluid source 610a (as described above for pressure-operated valve 270 (570) for FIGS. 2, 5A-5F) or the second fluid from the first upstream reservoir pump 660a, and also to, during operation, pass therethrough to the tubing 658b downstream of the second pressure-operated valve 670b, under a fourth pressure condition, the third IV fluid from the another upstream reservoir pump 660b (as described above for reservoir pump 260 (360, 360) for FIGS. 2, 3A-4B and pressure operated valve 270 (570) for FIGS. 2, 5A-5F), where the fourth pressure condition is a condition of higher pressure than the third pressure condition. For example, the third pressure may be the fluid pressure of gravity-fed first IV fluid entering second pressure-operated valve 670b via tubing 658a, and the fourth pressure may be the fluid pressure of pressurized third IV fluid from another reservoir pump 660b entering second pressure-operated valve 670b via tubing 656b. The third pressure may be the fluid pressure of pressurized second IV fluid from reservoir pump 660a entering second pressure-operated valve 670b via tubing 658a, and the fourth pressure may be the fluid pressure of pressurized third IV fluid from another reservoir pump 660b entering second pressure-operated valve 670b via tubing 656b.

Any suitable pressure-operated valve 670b may be utilized to selectively dispense the first IV fluid (e.g. gravity-fed from IV fluid bag 610a via tubing 658a), the second IV fluid (e.g. from reservoir pump 660a via first pressure-operated valve 670a and tubing 658a), or the third IV fluid (e.g. from another reservoir pump 660b via tubing 656b) to downstream tubing 658b based on a pressure condition within second pressure-operated valve 670b. In various embodiments, second pressure-operated valve 670b is set at a threshold pressure such that, when such threshold pressure is met and/or exceeded, third IV fluid (e.g. dispensed from another reservoir pump 660b via tubing 656b), rather than first IV fluid (e.g. gravity-fed from IV fluid bag 610a via tubing 658b), is passed therethrough and dispensed to downstream tubing 658b. In various embodiments, second pressure-operated valve 670b is set at a threshold pressure such that, when such threshold pressure is met and/or exceeded, third IV fluid (e.g. dispensed from another reservoir pump 660b via tubing 656b), rather than first IV fluid (e.g. gravity-fed from IV fluid bag 610a via tubing 658b) or second IV fluid (e.g. from reservoir pump 660a via first pressure-operated valve 670a and tubing 658a), is passed therethrough and dispensed to downstream tubing 658b. In various embodiments, the third pressure condition of second pressure-operated valve 670b is the same as the first pressure condition of first pressure-operated valve 670a.

Figure 7:
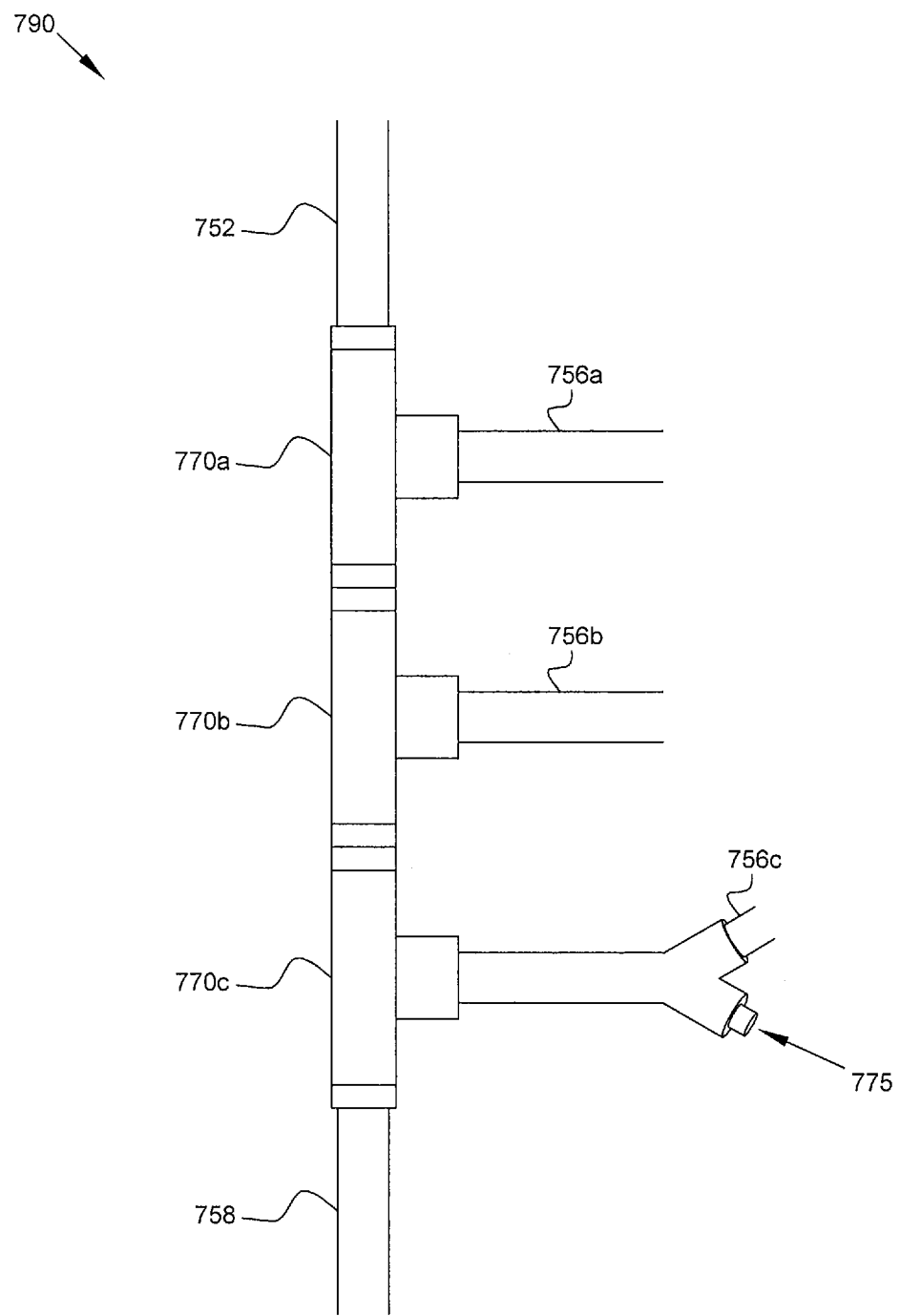
FIG. 7 is a plan view of an example of a manifold according to some embodiments.

Referring now to FIG. 7, a plan view of an example of a manifold according to some embodiments is provided. In various embodiments, manifold 790 includes a plurality of inter-connected pressure-operated valves (770a, 770b, 770c) that operate as described above for pressure-operated valve 270, first pressure-operated valve 670a, and/or second pressure-operated valve 670b for FIGS. 2, 5A-5F, and/or 6. In various embodiments, manifold 790 is connected to tubing 752 and tubing 756a via first pressure operated valve 770a, to tubing 756b via second pressure operated valve 770b, and to tubing 756c, tubing 758, and port (e.g. luer lock connector) 775, via third pressure operated valve 770c. In various embodiments, port 775 is configured to receive a needle of a syringe (not shown) as described above for port 575. In various embodiments, each of the plurality of inter-connected pressure-operated valves (770a, 770b, 770c) includes one or more respective check valves (not shown) such as, for example, as described above for pressure-operated valve 270 for FIGS. 5D-5F.

As shown in FIG. 7, third pressure operated valve 770c may be configured to operate in fluid communication with an upstream first source of first IV fluid (e.g. 610a) via tubing 752, first pressure operated valve 770a, and second pressure operated valve 770b, with a first upstream reservoir pump (e.g. reservoir pump 260 or 660a) via tubing 756a, first pressure operated valve 770a, and second pressure operated valve 770b, with a second upstream reservoir pump (e.g. reservoir pump 660b) via tubing 756b and second pressure operated valve 770b, with a syringe via port 775 (e.g. luer lock connector), and with a third upstream reservoir pump via tubing 756c. In various embodiments, third pressure operated valve 770c may be configured to, during operation, pass therethrough to tubing 758 downstream of the third pressure operated valve 770c, under a fifth pressure condition, the first IV fluid from the upstream first fluid source 610a (as described above for pressure-operated valve 270 (570) for FIGS. 2, 5A-5F) and also to, during operation, pass therethrough to the tubing 758 downstream of the third pressure operated valve 770c, under a sixth pressure condition, a fourth IV fluid from the syringe (as described above for reservoir pump 260 (360, 460) for FIGS. 2, 3A-4B and port connector 575 for FIGS. 5C, 5F), where the sixth pressure condition is a condition of higher pressure than the fifth pressure condition.

In various embodiments, third pressure operated valve 770c may be configured to, during operation, pass therethrough to tubing 758 downstream of the third pressure operated valve 770c, under a fifth pressure condition, the first IV fluid from the upstream first fluid source 610a (as described above for pressure-operated valve 270 (570) for FIGS. 2, 5A-5F), the second IV fluid from the first upstream reservoir pump (e.g. 260 or 660a), or the third IV fluid from the second upstream reservoir pump (e.g. 260 or 660b), and also to, during operation, pass therethrough to the tubing 758 downstream of the third pressure operated valve 770c, under a sixth pressure condition, a fourth IV fluid from the third upstream reservoir pump (e.g. 260) (as described above for reservoir pump 260 (360, 460) for FIGS. 2, 3A-4B and pressure-operated valve 270 (570) for FIGS. 2, 5A-5F), where the sixth pressure condition is a condition of higher pressure than the fifth pressure condition.

For example, the fifth pressure may be the fluid pressure of gravity-fed first IV fluid entering second pressure-operated valve 670b via tubing 658a, and the sixth pressure may be the fluid pressure of pressurized fourth IV fluid from the third upstream reservoir pump (not shown) entering third pressure-operated valve 770c via tubing 756c or of pressurized fourth IV fluid from a syringe (not shown) entering third pressure-operated valve 770c via port 775. The fifth pressure may be the fluid pressure of pressurized second IV fluid from the first upstream reservoir pump (e.g. 260 or 660a) entering manifold 700 via tubing 756a or pressurized third IV fluid from the second upstream reservoir pump (e.g. 260 or 660b) entering manifold 700 via tubing 756b, and the sixth pressure may be the fluid pressure of pressurized fourth IV fluid from the third upstream reservoir pump (not shown) entering third pressure-operated valve 770c via tubing 756c.

Figure 8:
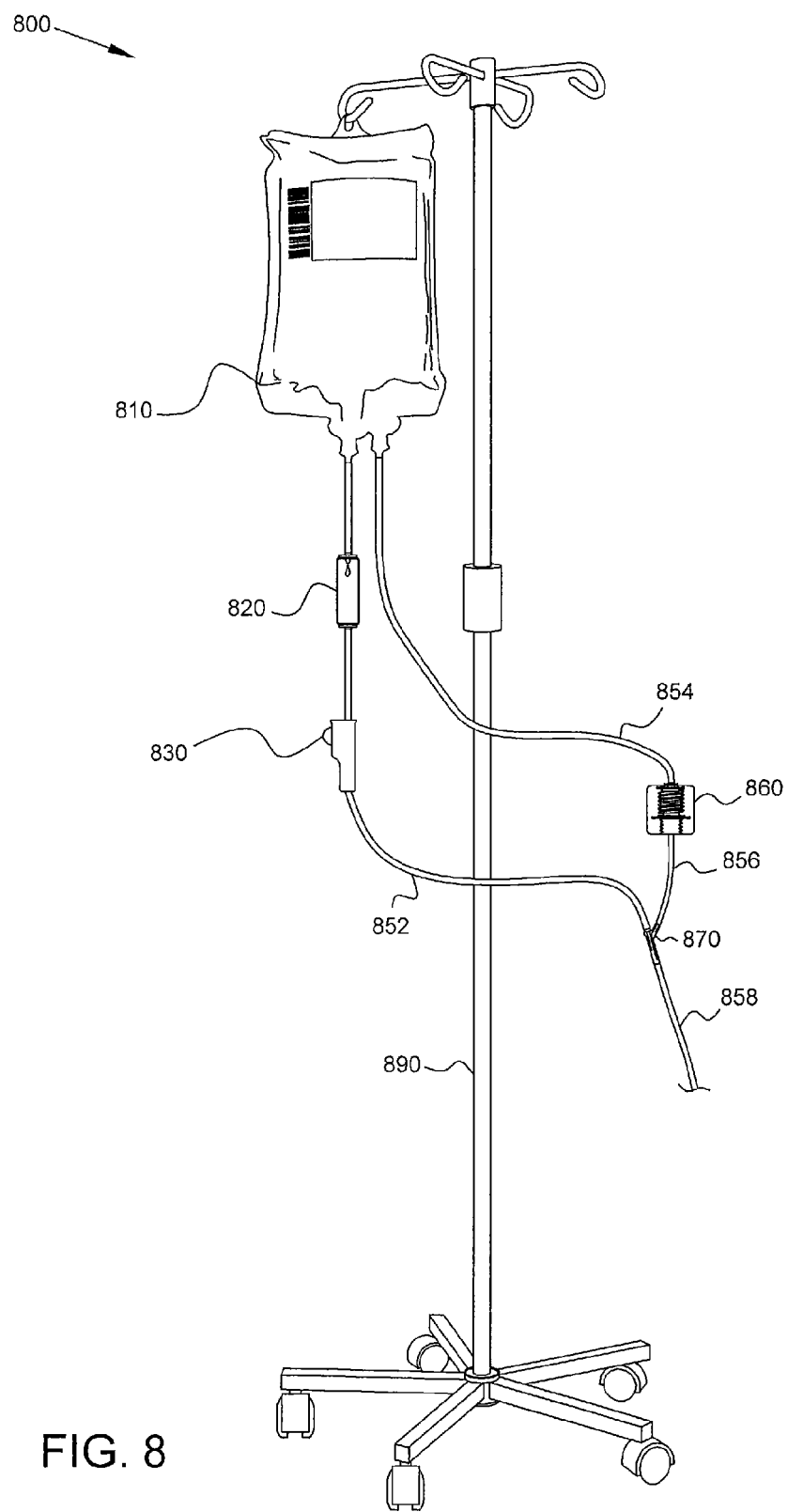
FIG. 8 is a perspective view of an intravenous (IV) fluid administration system according to some embodiments of the present disclosure.

With reference to FIG. 8, a perspective view of an intravenous (IV) fluid administration system according to some embodiments is provided. As illustrated in FIG. 8, some embodiments include a source of a first IV fluid 810, a drip chamber 820, a roller clamp 830, and tubing 852 downstream of roller clamp 830 as described above for FIG.

2. In various embodiments, IV fluid administration system 800 includes a pressure operated valve 870 as described above for pressure operated valve 270 (570) for FIGS. 2, 5A-5F. In various embodiments, IV fluid administration system 800 includes a reservoir pump 860, and tubing 856 between reservoir pump 860 and pressure operated valve 870, as described above for reservoir pump 260 (360, 360) for FIGS. 2, 3A-4B and pressure operated valve 270 (570) for FIGS. 2, 5A-5F. In various embodiments, IV fluid administration system 800 includes tubing 854 between reservoir pump 860 and a source of a IV fluid 810 for reservoir pump 860, as described above for reservoir pump 260 (360, 360) for FIGS. 2, 3A-4B. In various embodiments, first IV fluid source 810 and the IV fluid source of reservoir pump 860 (not shown) are different IV fluid sources as described above for FIG. 2. In the illustrated embodiments, first IV fluid source 810 and the IV fluid source of reservoir pump 860 are the same IV fluid source 810a. As shown in FIG. 8, IV fluid administration system 800 does not include a stopcock or an observation chamber between reservoir pump 860 and source of IV fluid 810 for reservoir pump 860.

Figure 9:
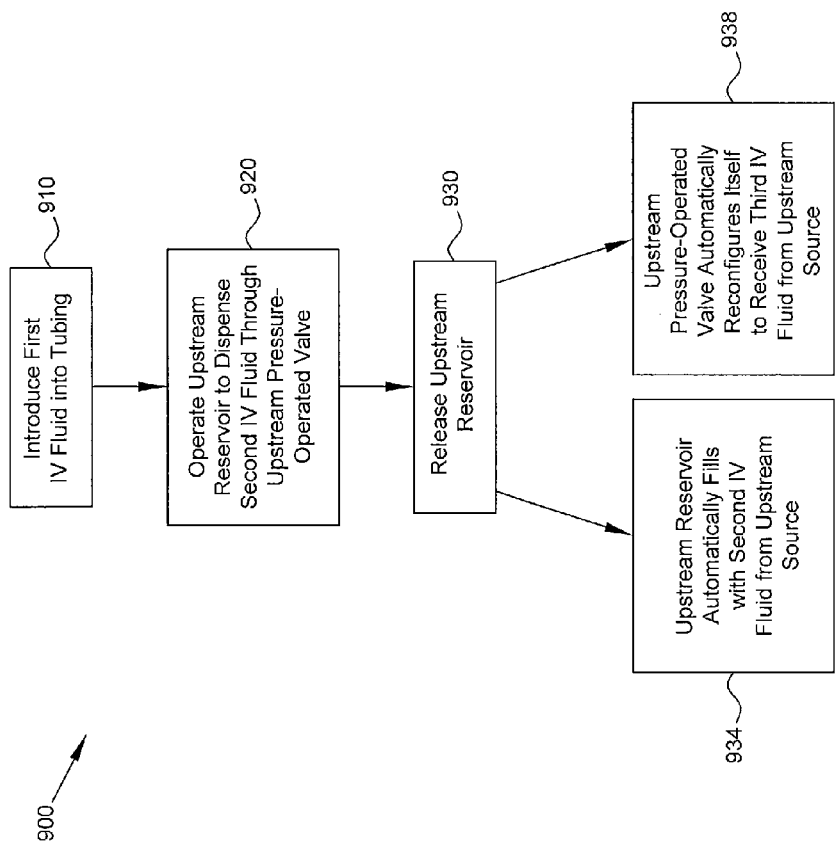
FIG. 9 is a flow chart illustrating a method of flushing a line of an intravenous fluid administration system according to some embodiments.

Referring now to FIG. 9, a flow chart illustrating a method 900 of flushing a line of an intravenous fluid administration system (e.g. IV fluid administration system 200, 600, 800) according to some embodiments is provided. At block 910, a first IV fluid is introduced into tubing (e.g. tubing 258, tubing 858) configured to transport fluid for intravenous infusion to a subject. At block 920, a reservoir pump (e.g. reservoir pump 260, reservoir pump 860), that is positioned upstream of the tubing (e.g. tubing 258, tubing 858), is operated to dispense a predetermined amount of a second IV fluid through a pressure-operated valve (e.g. pressure-operated valve 270, pressure-operated valve 870), that is also positioned upstream of the tubing (e.g. tubing 258, tubing 858), and at a fluid pressure exceeding a threshold pressure of the pressure-operated valve (e.g. pressure-operated valve 270, pressure-operated valve 870). At block 930, the reservoir pump (e.g. reservoir pump 260, reservoir pump 860) is released. At block 934, once released at block 930, the reservoir pump (e.g. reservoir pump 260, reservoir pump 860) automatically fills itself with the predetermined amount of the second IV fluid from a source (e.g. source 210, source 810) upstream of the reservoir pump (e.g. reservoir pump 260, reservoir pump 860). At block 938, once the reservoir pump (e.g. reservoir pump 260, reservoir pump 860) is released at block 930, the pressure-operated valve (e.g. pressure-operated valve 270, pressure-operated valve 870) automatically reconfigures itself to receive a third IV fluid from a fluid source (e.g. source 210, source 810) upstream of the pressure-operated valve (e.g. pressure-operated valve 270, pressure-operated valve 870) and at a fluid pressure less than the threshold pressure.

In various embodiments, the fluid source upstream of the reservoir pump (e.g. reservoir pump 260, reservoir pump 860) and the fluid source upstream of the pressure-operated valve (e.g. pressure-operated valve 270, pressure-operated valve 870) are the same source (e.g. source 210, source 810) and the second and third IV fluids are the same type of fluid. In various embodiment, the fluid source upstream of the reservoir pump (e.g. reservoir pump 260, reservoir pump 860) and the fluid source upstream of the pressure-operated valve (e.g. pressure-operated valve 270, pressure-operated valve 870) are different sources and the second and third IV fluids are different types of fluid. In various embodiments, the first IV fluid is introduced (at block 910) via an injection port (e.g. of port connector 575, port 775), or an inlet port (e.g. port 245) of a three-way stopcock (e.g. stopcock 240) that is disposed downstream of the pressure-operated valve (e.g. pressure-operated valve 270, pressure-operated valve 870). In various embodiments, the first IV fluid is introduced (at block 910) via an inlet port (e.g. port 575, port 775) of the pressure-operated valve (e.g. pressure-operated valve 270, pressure-operated valve 870) and at a pressure exceeding the threshold pressure of the pressure-operated valve (e.g. pressure-operated valve 270, pressure-operated valve 870). In various embodiments, the third IV fluid is a solution comprising saline and the first IV fluid comprises a drug or an antibiotic.

Figure 10A:
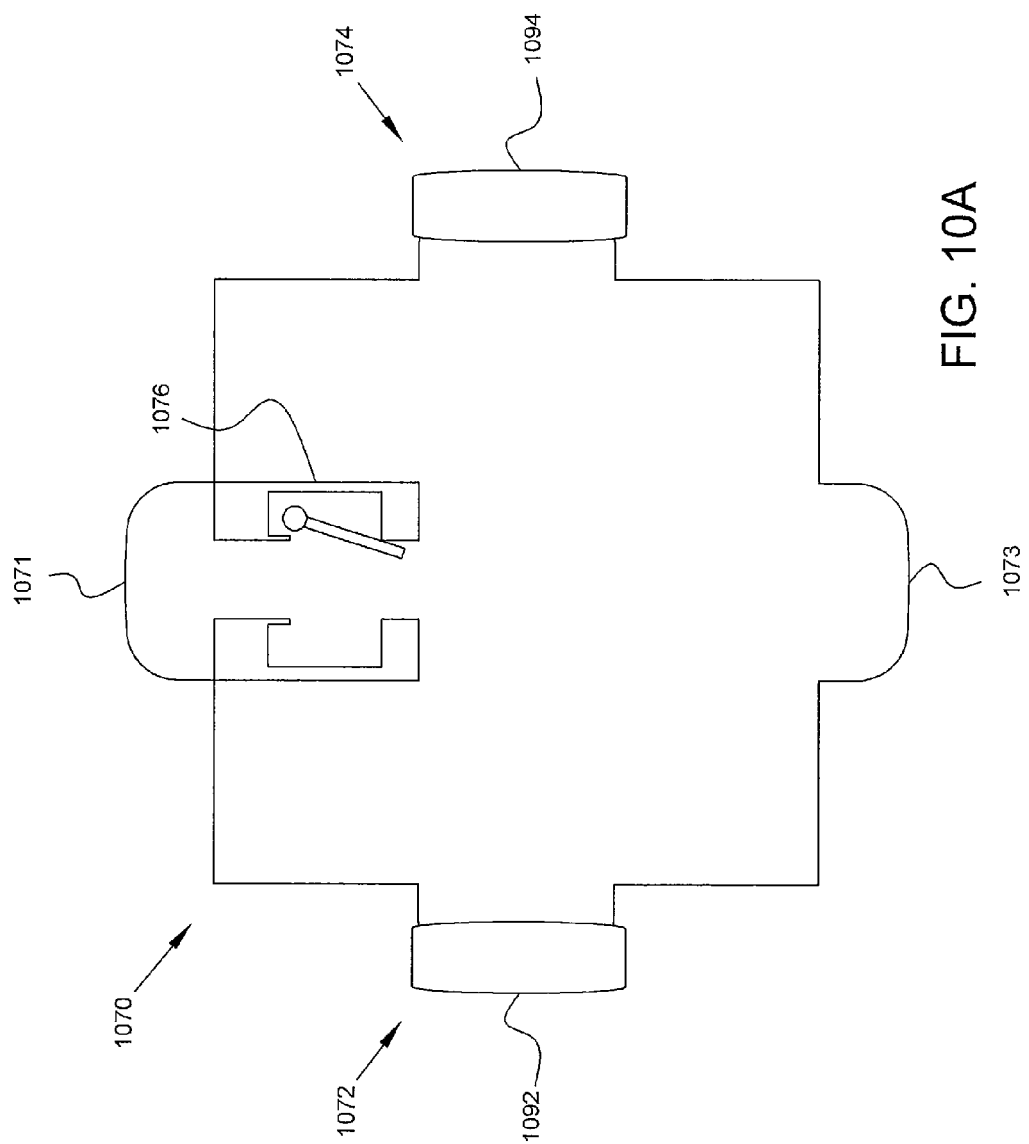
FIG. 10A is a plan view of an example of a chamber according to some embodiments of the present disclosure.
Figure 10B:
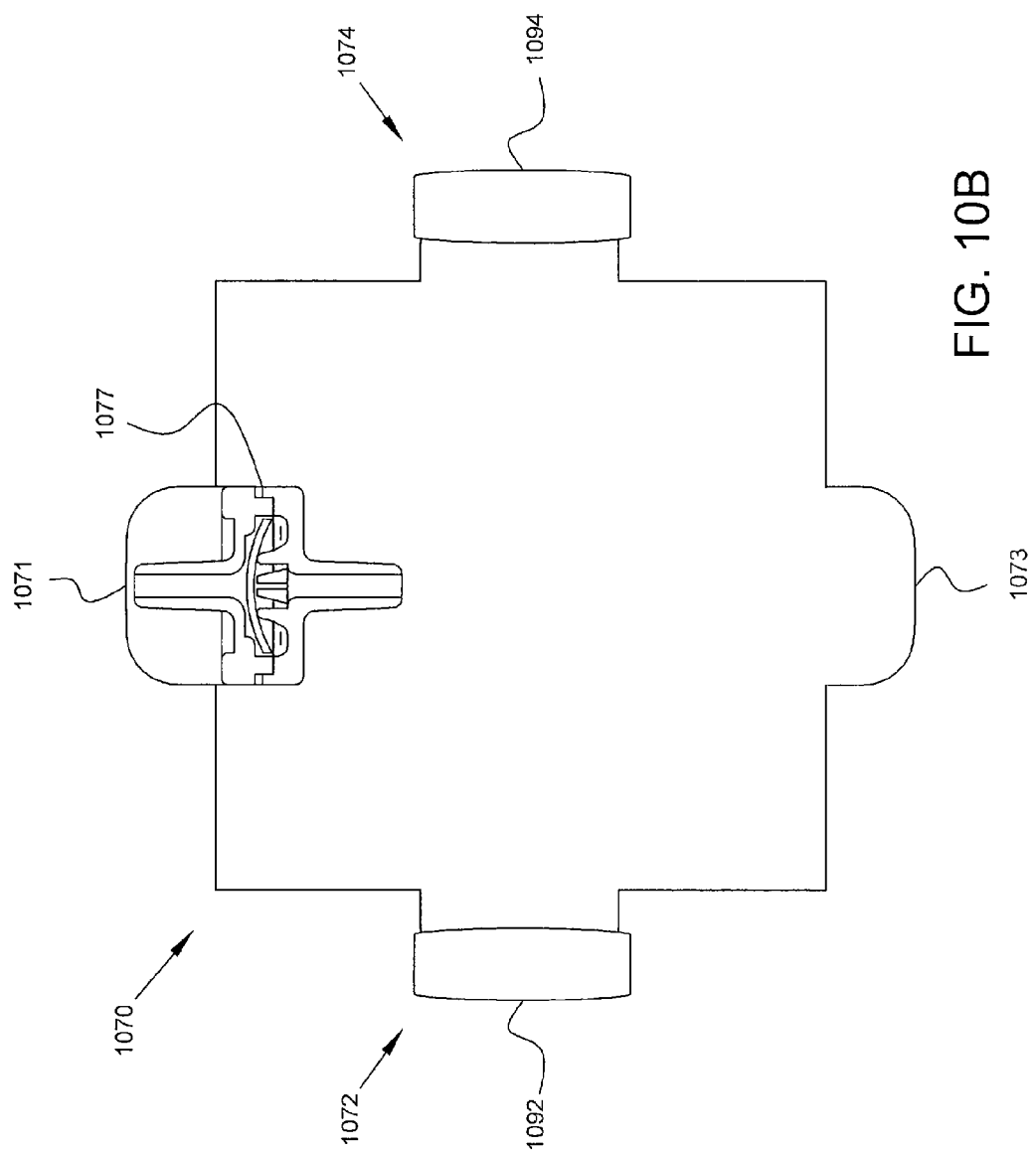
FIG. 10B is a plan view of an example of a chamber including a plurality of connector ports according to some embodiments of the present disclosure.

The inventor has observed that utilizing a chamber including a plurality of connector ports, where at least the connector port configured to receive fluid from a gravity-fed IV fluid source is automatically operated, the time and cost necessary for using stopcocks is eliminated. Referring now to FIGS. 10A and 10B, plan views of examples of a chamber according to some embodiments are provided. In various embodiments, a chamber 1070 is provided including a plurality of connector ports 1071, 1072, 1073, 1074. While the illustrated embodiments show an example of a chamber 1070 with four (4) connector ports, a chamber 1070 including any suitable number of connector ports (e.g. three (3), five (5), six (6), etc.) may be selected and utilized. As illustrated in the examples of FIGS. 10A and 10B, chamber 1070 may include a check valve 1076 downstream of connector port 1071. In the illustrated embodiments of FIG. 10A, check valve 1076 is a normally open swing check valve. In the illustrated embodiments of FIG. 10B, check valve 1076 is a normally open disc check valve. Any suitable check valve may be utilized for check valve 1076. For example, a swing check valve, lift check valve, wafer check valve, disc check valve, flapper check valve, inline check valve, ball check valve, etc. may be utilized.

Each of the plurality of connector ports (1071, 1072, 1073, 1074) is configured to be operably coupled to an end of tubing or a valve connector. In various embodiments, a connector port is configured to be operably coupled to a cover (e.g. a cap) to prevent contamination from entering chamber 1070 when the connector port is not otherwise operably coupled to an end of tubing or a valve connector. For example, a cap may be screwed or snapped onto any connector port that is not otherwise operably coupled to an end of tubing or a valve connector. Referring to FIGS. 10A and 10B, for example, connector port 1072 may be configured to be operably coupled to cap 1092, and connector port 1074 may be configured to be operably coupled to cap 1094.

Figure 10C:
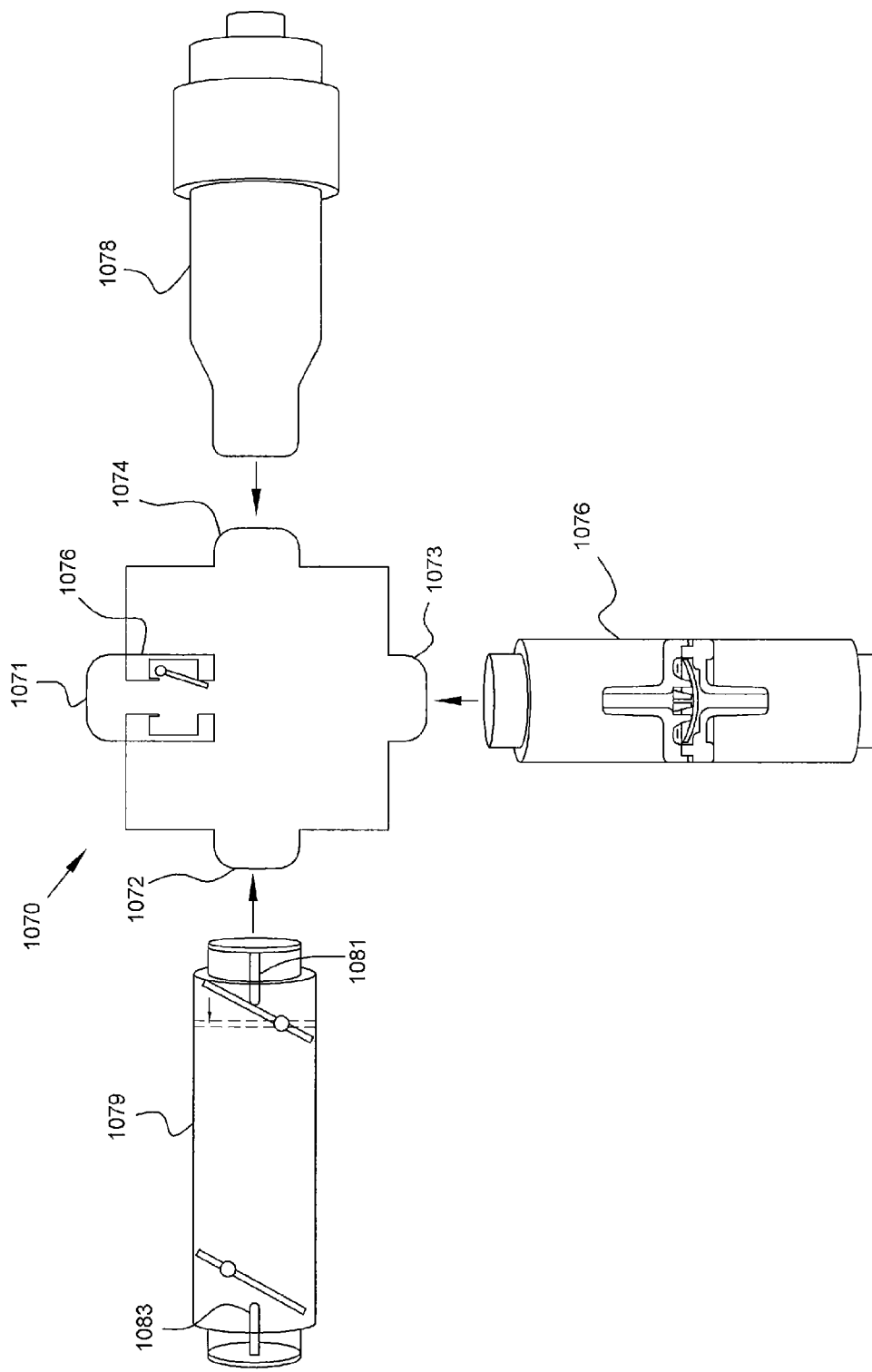
FIG. 10C is a plan view of an example of a chamber including a plurality of connector ports, and examples of valve connectors, according to some embodiments of the present disclosure.

Referring now to FIG. 10C, a plan view of an example of a chamber including a plurality of connector ports, and examples of valve connectors, according to some embodiments is provided. As illustrated in the example of FIG. 10C, an end of a valve connector 1078 including a needle-free valve may be operably coupled to a connector port (e.g. 1074), an end of valve connector 1076, including one or more normally open check valves, may be operably coupled to a connector port (e.g. 1073), and/or an end of valve connector 1079, including a normally open check valve and/or a normally closed check valve, may be operably coupled to a connector port (e.g. 1072), of chamber 1070. Any suitable valve connector may be operably coupled to a connector port of chamber 1070. For example, the valve connector may include a needle-free valve, an aspiration valve, a trumpet valve, a normally closed check valve, a normally open check valve, a luer, and/or combinations thereof.

In various embodiments, the valve connector (e.g. 1079, FIG. 10C) may include a normally open check valve at one end and a normally closed check valve at the other end. In various embodiments, engagement of one end of the valve connector with a connector port of chamber 1070 will automatically reposition the respective check valve at such end such that normally open check valve will be closed and normally closed valve will be opened. For example, valve connector 1079 (FIG. 10C) includes a normally open check valve at one end, a normally closed check valve at the other end, a post 1081, and a post 1083. During operation, if an operator (e.g. a clinician) desires that both of the check valves in such a valve connector (e.g. 1079, FIG. 10C) be operated in a normally open position, the operator will operably couple the end of the valve connector (e.g. 1079, FIG. 10C) with the normally closed check valve to a connector port of chamber 1070. Engagement of such end with a connector port will operate post 1081 to open the normally closed check valve. In the illustrated example of FIG. 10C, post 1081 will contact the hinged disc assembly and apply a force to open the normally closed check valve as the respective end of the valve connector is engaged with the connector port. During operation, if an operator (e.g. a clinician) desires that both of the check valves in such a valve connector (e.g. 1079, FIG. 10C) be operated in a normally closed position, the operator will operably couple the end of the valve connector (e.g. 1079, FIG. 10C) with the normally open check valve to a connector port of chamber 1070. Engagement of such end with a connector port will operate post 1083 to close the normally open check valve. In the illustrated embodiments of FIG. 10C, post 1083 will contact the hinged disc assembly and apply a force to close the normally open check valve as the respective end of the valve connector is engaged with the connector port.

In various embodiments, a plurality of the connector ports are respectively, operably, coupled to a respective end of tubing or a respective valve connector. For example, a respective end of tubing or valve connector may be clamped, screwed, or snapped, on or into each of the plurality of connector ports. A locking collar may be used to operably couple a respective end of tubing or valve connector with one or more of the plurality of connector ports. In various embodiments, each of the plurality of connector ports includes a respective male and/or female end to connect to an end of tubing or a valve connector. In some embodiments, a respective male and/or female adapter may be utilized to connect of each the plurality of connector ports (1071, 1072, 1073, 1074) to an end of tubing or a valve connector. In some embodiments, one or more of the plurality of connector ports are shaped to achieve a snap-on and snap-off engagement with ends of valve connectors.

Figure 10D:
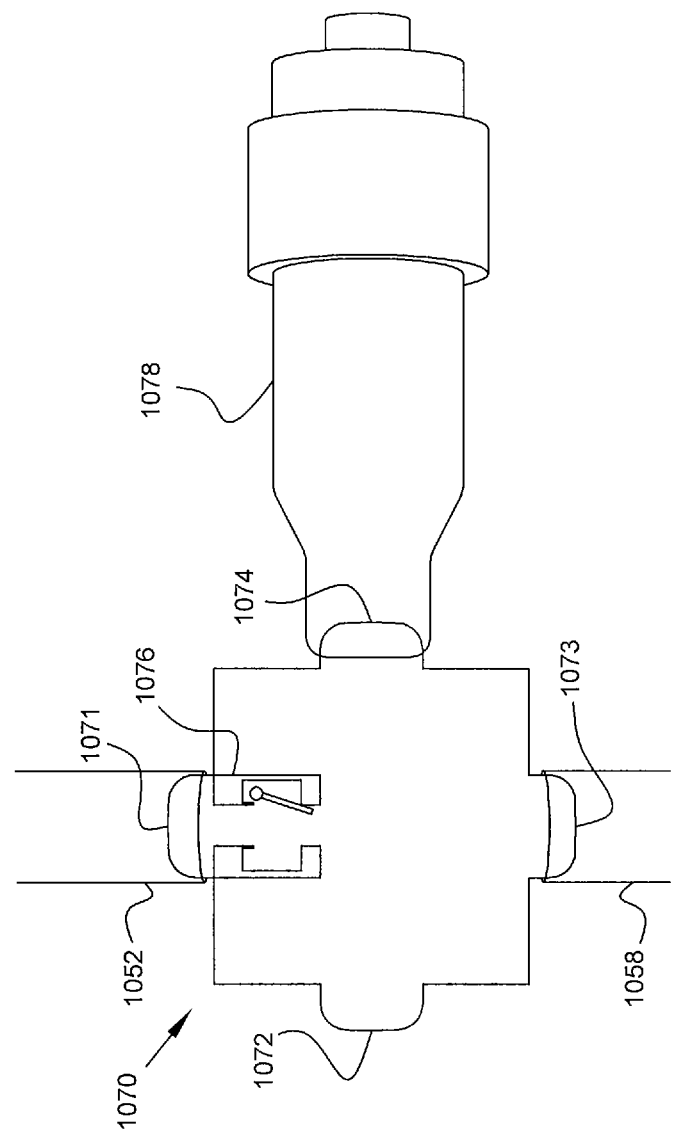
FIG. 10D is a plan view of an example of a chamber including a plurality of connector ports respectively connected to ends of tubing and an example of a valve connector according to some embodiments of the present disclosure.
Figure 10E:
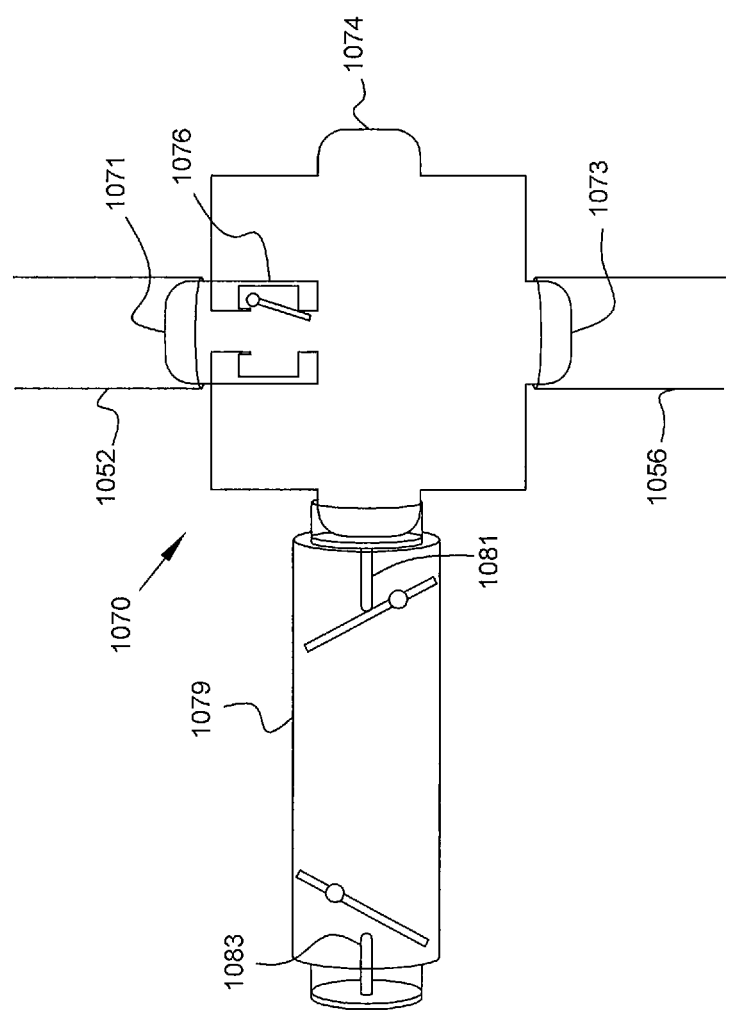
FIG. 10E is a plan view of an example of a chamber including a plurality of connector ports respectively connected to ends of tubing and an example of a valve connector according to some embodiments of the present disclosure.

With reference to FIGS. 10D and 10E, plan views of examples of a chamber including a plurality of connector ports respectively connected to ends of tubing and examples of valve connectors according to some embodiments are provided. As illustrated in the example of FIG. 10D, an end of a valve connector 1078 including a needle-free valve may be operably coupled to connector port 1074, an end of tubing 1052 may be operably coupled to connector port 1071, and an end of tubing 1058 may be operably coupled to connector port 1073, of chamber 1070. As illustrated in the example of FIG. 10E, an end of valve connector 1079, including a normally closed check valve, may be operably coupled to connector port 1074, an end of tubing 1052 may be operably coupled to connector port 1073, and an end of tubing 1058 may be operably coupled to connector port 1073, of chamber 1070. In the illustrated example of FIG. 10E, post 1081 of valve connector 1079 contacts the hinged disc assembly and applies a force to open the normally closed check valve as the respective end of the valve connector 1079 is engaged with the connector port 1072.

Figure 10F:
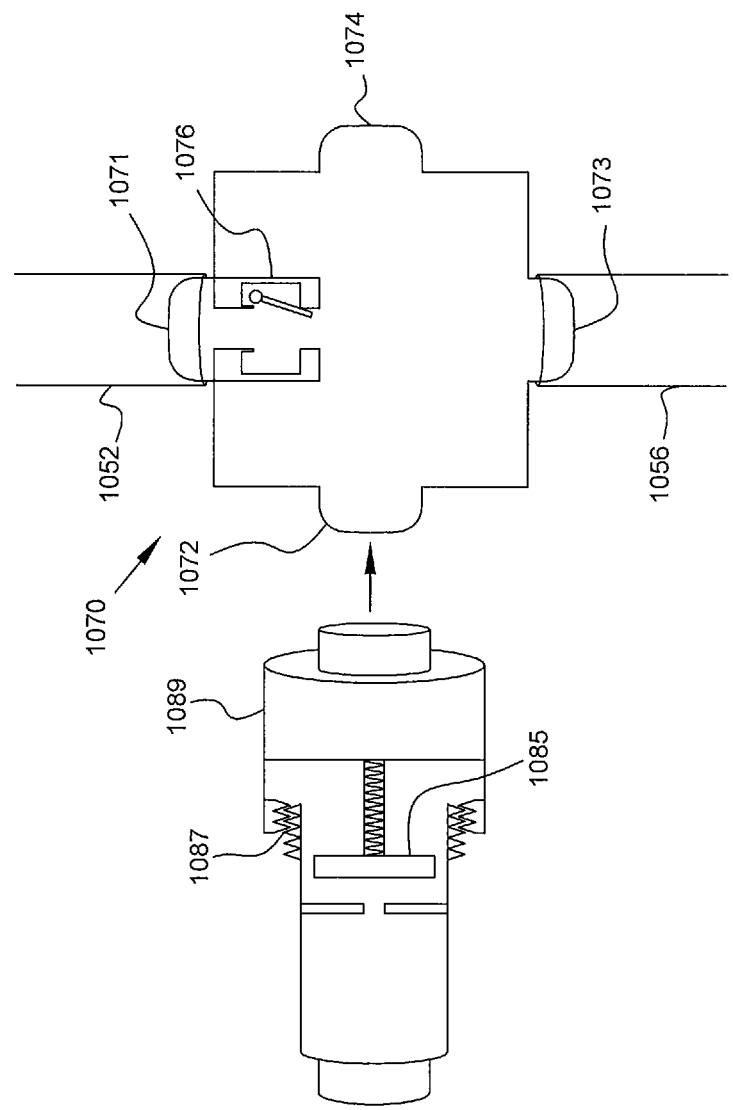
FIG. 10F is a plan view of an example of a chamber including a plurality of connector ports respectively connected to ends of tubing and an example of a valve connector according to some embodiments of the present disclosure.
Figure 10G:
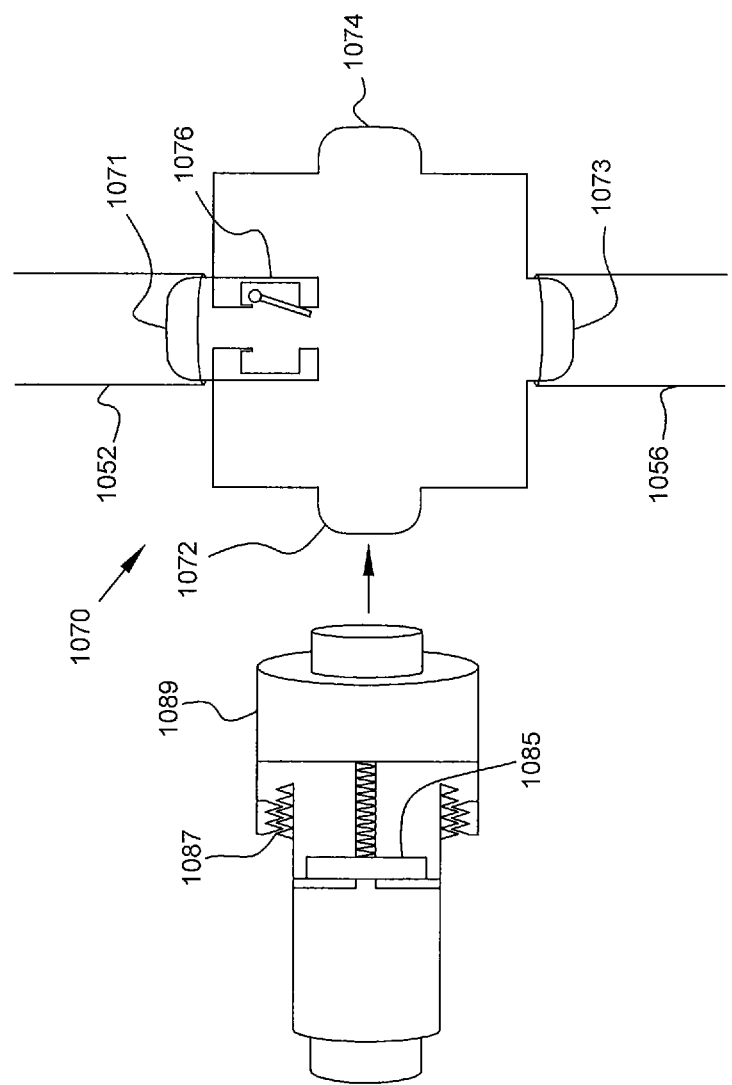
FIG. 10G is a plan view of an example of a chamber including a plurality of connector ports respectively connected to ends of tubing and an example of a valve connector according to some embodiments of the present disclosure.

With reference to FIGS. 10F and 10G, plan views of examples of a chamber including a plurality of connector ports respectively connected to ends of tubing and examples of valve connectors according to some embodiments are provided. In various embodiments, a first part of valve connector may operably engage a second part of valve connector 1089. As illustrated in the examples of FIGS. 10F and 10G, a valve connector 1089 may include a first part with a larger circumference than a circumference of a second part. In the illustrated examples, a portion of the first part is internally threaded to threadably engage 1067 an externally threaded portion of the second part. Any suitable technique for operable engagement between the first and second part of valve connector 1089 may be utilized. For example, one or both of the first and second parts of valve connector 1089 may include a notch, ridge, rib, and/or threads to permit an operator to operate the valve connector between a first and a second position. In various embodiments, the first part of valve connector 1089 may be operated between the first position and the second position by twisting the first part in a counter-clockwise or clockwise direction relative to the second part. In some embodiments, a full rotation of a portion of the first part around a portion of second part is required to operate the valve connector between a first position and a second position. In some embodiments, a partial rotation (e.g. ¼ rotation, ½ rotation) is required. In some embodiments, a plurality of full rotations are required. In some embodiments, a first part is pushed toward a second part and then twisted relative to the second part to operate the valve connector 1089 between a first position and a second position.

In the illustrated example of FIG. 10F, valve connector 1089 is in a first position such that a check valve including plunger assembly 1085 is a normally open check valve. In the illustrated example, the proximal end of valve connector 1089 (relative to chamber 1070) may be operably coupled to connector port 1072 and the distal end of valve connector 1089 may be operably coupled to an end of tubing to receive IV fluid from an upstream source. In the illustrated example, with the proximal end of valve connector 1089 operably coupled to connector port 1072, IV fluid from an upstream source is permitted to flow through valve connector 1089 and past plunger assembly 1085 into chamber 1070 via connector port 1072. In the illustrated example, with the proximal end of valve connector 1089 operably coupled to connector port 1072, fluid pressure of IV fluid received into chamber 1070 via another connector port (e.g. 1071, 1074, 1073) may operate to shut the normally open check valve in valve connector 1089 by operating plunger assembly 1085 to prevent the IV fluid from flowing toward the distal end (relative chamber 1070) of valve connector 1089.

Referring now to the illustrated example of FIG. 10G, valve connector 1089 has been operated from the first position (illustrated in FIG. 10F) to a second position (illustrated in FIG. 10G) such that the check valve including plunger assembly 1085 is a normally closed check valve. In the illustrated example, the proximal end of valve connector 1089 (relative to chamber 1070) may be operably coupled to connector port 1072 and the distal end of valve connector 1089 may be operably coupled to an end of tubing to receive IV fluid from an upstream source. In the illustrated example, with the proximal end of valve connector 1089 operably coupled to connector port 1072, IV fluid from an upstream source and received via the distal end (relative chamber 1070) of valve connector 1089 is prevented from flowing through valve connector 1089 and past plunger assembly 1085 into chamber 1070 via connector port 1072 until the fluid pressure of such IV fluid exceeds a threshold biasing pressure of the spring of plunger assembly 1085. In the illustrated example, with the proximal end of valve connector 1089 operably coupled to connector port 1072, plunger assembly 1085 also prevents IV fluid received into chamber 1070 via another connector port (e.g. 1071, 1074, 1073) from flowing toward the distal end (relative chamber 1070) of valve connector 1089.

In various embodiments, chamber 1070 is configured to operate in fluid communication with an upstream first source of a first IV fluid (e.g. FIG. 2 source 210, FIG. 8 source 810) via a first one (e.g. 1071) of the plurality of connector ports of chamber 1070. Any suitable fluid for intravenous administration to a subject may be provided as the first IV fluid as described above for first IV fluid source of FIG. 2. In various embodiments, an end of tubing (e.g. FIG. 2 tubing 252, FIG. 8 tubing 852) may be operably coupled to connector port 1071 of chamber 1070 such that chamber 1070 receives the first IV fluid gravity fed from the first IV fluid source (e.g. FIG. 2 source 210, FIG. 8 source 810) via connector port 1071.

In various embodiments, chamber 1070 is configured to, during operation, pass therethrough the chamber 1070 to tubing downstream (e.g. FIG. 2 tubing 258, FIG. 8 tubing 858) of the chamber 1070, under a first pressure condition, the first IV fluid from the upstream first IV fluid source (e.g. FIG. 2 source 210, FIG. 8 source 810) via a second one (e.g. 1073) of the plurality of connector ports 1071, 1072, 1073, 1074. In various embodiments, an end of tubing (e.g. FIG. 2 tubing 258, FIG. 8 tubing 858) may be operably coupled to connector port 1073 of chamber 1070, and an end of tubing (e.g. FIG. 2 tubing 252, FIG. 8 tubing 852) may be operably coupled to connector port 1071 of chamber 1070. In various embodiments, during operation and under a first pressure condition (e.g. the first pressure may be the fluid pressure of gravity-fed first IV fluid entering chamber 1070 via tubing 252, 852 and connector port 1071), chamber 1070 may pass therethrough the first IV fluid gravity fed from the first IV fluid source (e.g. FIG. 2 source 210, FIG. 8 source 810) to tubing downstream (e.g. FIG. 2 tubing 258, FIG. 8 tubing 858) of the chamber 1070 via connector ports 1071 and 1073.

In various embodiments, a third one (e.g. 1072) of the plurality of connector ports of chamber 1070 is configured to connect to an end of tubing or a valve connector such that, during operation, the chamber 1070 is configured to, under a second pressure condition higher than the first pressure condition, pass therethrough, to the tubing downstream (e.g. FIG. 2 tubing 258, FIG. 8 tubing 858) of the chamber 1070, a second IV fluid from a second IV fluid source via the third (e.g. 1072) and second (e.g. 1073) connector ports, to prevent flow of the first IV fluid into the tubing downstream (e.g. FIG. 2 tubing 258, FIG. 8 tubing 858) of the chamber 1070, and to prevent flow of the second IV fluid through the first connector port (e.g. 1071). In various embodiments, an end of tubing (e.g. FIG. 2 tubing 256, FIG. 8 tubing 856) may be operably coupled to connector port 1072, an end of tubing (e.g. FIG. 2 tubing 258, FIG. 8 tubing 858) may be operably coupled to connector port 1073, and an end of tubing (e.g. FIG. 2 tubing 252, FIG. 8 tubing 852) may be operably coupled to connector port 1071, of chamber 1070. In some embodiments, an end of a valve connector including a normally closed check valve (e.g. 1079) may be operably coupled to connector port 1072 and an end of tubing (e.g. FIG. 2 tubing 256, FIG. 8 tubing 856) may be operably coupled to the other end of the valve connector (e.g. 1079).

In various embodiments, the tubing (e.g. FIG. 2 tubing 256, FIG. 8 tubing 856), or the valve connector (e.g. 1079), operably coupled to connector port 1072 is also operably coupled to a reservoir pump (e.g. FIG. 2 reservoir pump 260, FIG. 8 reservoir pump 860) configured to automatically refill itself with second IV fluid from a second upstream fluid source. In various embodiments, the first IV fluid source (e.g. FIG. 6 source 610*a*) and the IV fluid source (e.g. FIG. 6 source 610*b*) of the reservoir pump (e.g. FIG. 6 reservoir pump 660*b*) are different IV fluid sources as described above for FIGS. 2 and 6. In various embodiments, the first IV fluid source (e.g. FIG. 2 source 210, FIG. 8 source 810) and the IV fluid source of the reservoir pump (e.g. FIG. 2 reservoir pump 260, FIG. 8 reservoir pump 860) are the same IV fluid source (e.g. FIG. 2 source 210, FIG. 8 source 810) as described above for FIGS. 2 and 8.

In various embodiments, during a reservoir pump-use operation (e.g. a flushing operation), pressurized second IV fluid is received from a reservoir pump (e.g. FIG. 2 reservoir pump 260, FIG. 8 reservoir pump 860) and into chamber 1070 via tubing (e.g. FIG. 2 tubing 256, FIG. 8 tubing 856) operably coupled to a connector port (e.g. 1072, 1074) and such connector port. In various embodiments, the pressurized second IV fluid applies a fluid pressure to shut check valve 1076 of chamber 1070 as described above for check valves 366*a*, 466*a*, 576 for FIGS. 3B, 3D, 4A, 4B, 5E. In some embodiments, an end of a valve connector including a normally closed check valve (e.g. 1079) may be operably coupled to the selected connector port (e.g. 1072, 1074) and the end of tubing (e.g. FIG. 2 tubing 256, FIG. 8 tubing 856) may be operably coupled to the other end of the valve connector (e.g. 1079). In various embodiments, the pressurized second IV fluid applies a fluid pressure to open the normally closed check valve of the valve connector (e.g. 1079) as described above for check valves 366*b*, 466*b* for FIGS. 3B, 3D, 4A, and 4B.

In various embodiments, when the fluid pressure of the second IV fluid, received from a reservoir pump (e.g. FIG. 2 reservoir pump 260, FIG. 8 reservoir pump 860) via tubing (e.g. FIG. 2 tubing 256, FIG. 8 tubing 856) and the selected connector port (e.g. 1072, 1074), is at or exceeds a threshold pressure of check valve 1076, check valve 1076 shuts to block first IV fluid flow from upstream tubing (e.g. FIG. 2 tubing 252, FIG. 8 tubing 852) and the selected connector port (e.g. 1071), and to provide second IV fluid communication between the inlet from the selected connector port (e.g. 1072, 1074) and upstream tubing (e.g. FIG. 2 tubing 256, FIG. 8 tubing 856) and the outlet to downstream tubing (e.g. FIG. 2 tubing 258, FIG. 8 tubing 858) via selected connector port (e.g. 1073). When the fluid pressure received from reservoir pump (e.g. FIG. 2 reservoir pump 260, FIG. 8 reservoir pump 860) via tubing (e.g. FIG. 2 tubing 256, FIG. 8 tubing 856) and the selected connector port (e.g. 1072, 1074) is again less than the threshold pressure of check valve 1076, check valve 1076 re-opens to re-open the inlet from upstream tubing (e.g. FIG. 2 tubing 252, FIG. 8 tubing 852) and the selected connector port (e.g. 1071), and provide first IV fluid communication between the inlet from upstream tubing (e.g. FIG. 2 tubing 252, FIG. 8 tubing 852) and the selected connector port (e.g. 1071) and the outlet to downstream tubing (e.g. FIG. 2 tubing 258, FIG. 8 tubing 858) via selected connector port (e.g. 1073).

In various embodiments, an end of a valve connector including a needle free valve (e.g. 1078) or a luer lock (not shown) may be operably coupled to connector port 1074, an end of tubing (e.g. FIG. 2 tubing 258, FIG. 8 tubing 858) may be operably coupled to connector port 1073, and an end of tubing (e.g. FIG. 2 tubing 252, FIG. 8 tubing 852) may be operably coupled to connector port 1071, of chamber 1070. In various embodiments, pressurized second IV fluid injected via a syringe (not shown) inserted into a male luer in the valve connector (e.g. 1078) (including a needle free valve or a luer lock), and into chamber 1070 via the selected connector port (e.g. 1072, 1074), may apply a fluid pressure to shut check valve 1076 of chamber 1070 as described above for check valves 366a, 466a, 576 for FIGS. 3B, 3D, 4A, 4B, 5E.

In various embodiments, when the fluid pressure of the second IV fluid, received from a syringe (not shown) inserted into a male luer of the valve connector (e.g. 1078) (including a needle free valve or a luer lock) via the selected connector port (e.g. 1072, 1074), is at or exceeds a threshold pressure of check valve 1076, check valve 1076 shuts to block first IV fluid flow from upstream tubing (e.g. FIG. 2 tubing 252, FIG. 8 tubing 852) and the selected connector port (e.g. 1071), and to provide second IV fluid communication between the valve connector inlet via the selected connector port (e.g. 1072, 1074) and the outlet to downstream tubing (e.g. FIG. 2 tubing 258, FIG. 8 tubing 858) via selected connector port (e.g. 1073). When the fluid pressure received from the valve connector via selected connector port (e.g. 1072, 1074) is again less than the threshold pressure of check valve 1076, check valve 1076 re-opens to re-open the inlet from upstream tubing (e.g. FIG. 2 tubing 252, FIG. 8 tubing 852) and the selected connector port (e.g. 1071), and provide first IV fluid communication between the inlet from upstream tubing (e.g. FIG. 2 tubing 252, FIG. 8 tubing 852) and the selected connector port (e.g. 1071) and the outlet to downstream tubing (e.g. FIG. 2 tubing 258, FIG. 8 tubing 858) via selected connector port (e.g. 1073). In various embodiments, subsequent to injecting second IV fluid into chamber 1070 via the valve connector including a needle free valve (e.g. 1078) or a luer lock (not shown) and the selected connector port (e.g. 1072, 1074), a flushing operation using reservoir pump (e.g. FIG. 2 reservoir pump 260, FIG. 8 reservoir pump 860) can be initiated via tubing (e.g. FIG. 2 tubing 256, FIG. 8 tubing 856) and another selected connector port (e.g. 1074, 1072) as described above.

In various embodiments, a fourth one (e.g. 1074) of the plurality of connector ports of chamber 1070 is configured to connect to an end of tubing or a valve connector such that, during operation, the chamber 1070 is configured to, under a third pressure condition higher than the first pressure condition, pass therethrough, to the tubing downstream (e.g. FIG. 2 tubing 258, FIG. 8 tubing 858) of the chamber 1070, a third IV fluid from a third IV fluid source via the fourth (e.g. 1074) and second (e.g. 1073) connector ports, to prevent flow of the first IV fluid into the tubing downstream (e.g. FIG. 2 tubing 258, FIG. 8 tubing 858) of the chamber 1070, and to prevent flow of the third IV fluid through the first connector port (e.g. 1071). In various embodiments, an end of tubing (e.g. FIG. 2 tubing 256, FIG. 8 tubing 856) may be operably coupled to the selected connector port 1074, an end of tubing (e.g. FIG. 2 tubing 258, FIG. 8 tubing 858) may be operably coupled to connector port 1073, and an end of tubing (e.g. FIG. 2 tubing 252, FIG. 8 tubing 852) may be operably coupled to connector port 1071, of chamber 1070. In some embodiments, an end of a valve connector including a normally closed check valve (e.g. 1079) may be operably coupled to the selected connector port 1074 and an end of tubing (e.g. FIG. 2 tubing 256, FIG. 8 tubing 856) may be operably coupled to the other end of the valve connector (e.g. 1079).

In some embodiments, an end of tubing (e.g. FIG. 6 tubing 656a) may be operably coupled to the selected connector port 1074, an end of tubing (e.g. FIG. 6 tubing 656b) may be operably coupled to connector port 1072, an end of tubing (e.g. FIG. 6 tubing 652) may be operably coupled to connector port 1071, and an end of tubing (e.g. FIG. 6 tubing 658b) may be operably coupled to connector port 1073, of chamber 1070. In some embodiments, a plurality of connector ports of chamber 1070 can receive respective gravity-fed IV fluids from respective IV fluid sources. For example, an end of tubing (e.g. FIG. 2 tubing 252, FIG. 8 tubing 852) may be operably coupled to connector port 1071 to receive a first IV fluid gravity-fed from an IV fluid source (e.g. FIG. 2 IV fluid bag 210, FIG. 8 IV fluid bag 810) via connector port 1071 and check valve 1076, and another end of tubing (not shown) may be operably coupled to another selected connector port (e.g. 1074) to receive a second IV fluid gravity-fed from another IV fluid source (not shown) via the another selected connector port (e.g. 1074). In some embodiments, the another end of tubing (not shown) may be operably coupled to the another selected connector port (e.g. 1074) via a valve connector. In some embodiments, the valve connector may include a check valve (e.g. a normally open check valve).

In some embodiments, an end of tubing (e.g. FIG. 2 tubing 252, FIG. 8 tubing 852) may be operably coupled to connector port 1071 to receive a first IV fluid gravity-fed from an IV fluid source (e.g. FIG. 2 IV fluid bag 210, FIG. 8 IV fluid bag 810) via connector port 1071 and check valve 1076, another end of tubing (not shown) may be operably coupled to connector port 1074 to receive a second IV fluid gravity-fed from another IV fluid source (not shown) via connector port 1074 and a valve connector including a normally open check valve, an end of tubing (e.g. FIG. 2 tubing 258, FIG. 8 tubing 858) may be operably coupled to connector port 1073, and an end of tubing (e.g. FIG. 2 tubing 256, FIG. 8 tubing 856) may be operably coupled to the selected connector port 1074. In various embodiments, during a reservoir pump-use operation (e.g. a flushing operation), pressurized third IV fluid is received from a reservoir pump (e.g. FIG. 2 reservoir pump 260, FIG. 8 reservoir pump 860) and into chamber 1070 via tubing (e.g. FIG. 2 tubing 256, FIG. 8 tubing 856) operably coupled to connector port 1072 and such connector port 1072. In various embodiments, the pressurized third IV fluid applies a fluid pressure to shut check valve 1076 of chamber 1070, and the check valve in the valve connector operably coupled to connector port 1074, as described above for check valves 366a, 466a, 576 for FIGS. 3B, 3D, 4A, 4B, 5E. In various embodiments, when the fluid pressure of the third IV fluid, received from a reservoir pump (e.g. FIG. 2 reservoir pump 260, FIG. 8 reservoir pump 860) via tubing (e.g. FIG. 2 tubing 256, FIG. 8 tubing 856) and connector port 1072, is at or exceeds a respective threshold pressure of check valve 1076 and the check valve in the valve connector operably coupled to connector port 1074, such check valves respectively shut to block first IV fluid flow from upstream tubing (e.g. FIG. 2 tubing 252, FIG. 8 tubing 852) and connector port 1071 and to block second IV fluid flow from the upstream tubing operably coupled to connector port 1074, and to provide second IV fluid communication between the inlet from connector port 1072 and upstream tubing (e.g. FIG. 2 tubing 256, FIG. 8 tubing 856) and the outlet to downstream tubing (e.g. FIG. 2 tubing 258, FIG. 8 tubing 858) via connector port 1073. When the fluid pressure received from reservoir pump (e.g. FIG. 2 reservoir pump 260, FIG. 8 reservoir pump 860) via tubing (e.g. FIG. 2 tubing 256, FIG. 8 tubing 856) and connector port 1072 is again less than the respective threshold pressure of check valve 1076 and the check valve in the valve connector operably coupled to connector port 1074, such check valves re-open to re-open the inlet from upstream tubing (e.g. FIG. 2 tubing 252, FIG. 8 tubing 852) and connector port 1071 and the inlet from the upstream tubing operably coupled to connector port 1074, and provide respective first IV fluid and second IV fluid communication between the respective inlets and the outlet to downstream tubing (e.g. FIG. 2 tubing 258, FIG. 8 tubing 858).

In some embodiments, an end of tubing (e.g. FIG. 2 tubing 256, FIG. 8 tubing 856) may be operably coupled to the selected connector port 1074, an end of a valve connector including a needle free valve (e.g. 1078) or a luer lock (not shown) may be operably coupled to connector port 1072, an end of tubing (e.g. FIG. 2 tubing 258, FIG. 8 tubing 858) may be operably coupled to connector port 1073, and an end of tubing (e.g. FIG. 2 tubing 252, FIG. 8 tubing 852) may be operably coupled to connector port 1071, of chamber 1070.

Figure 11:
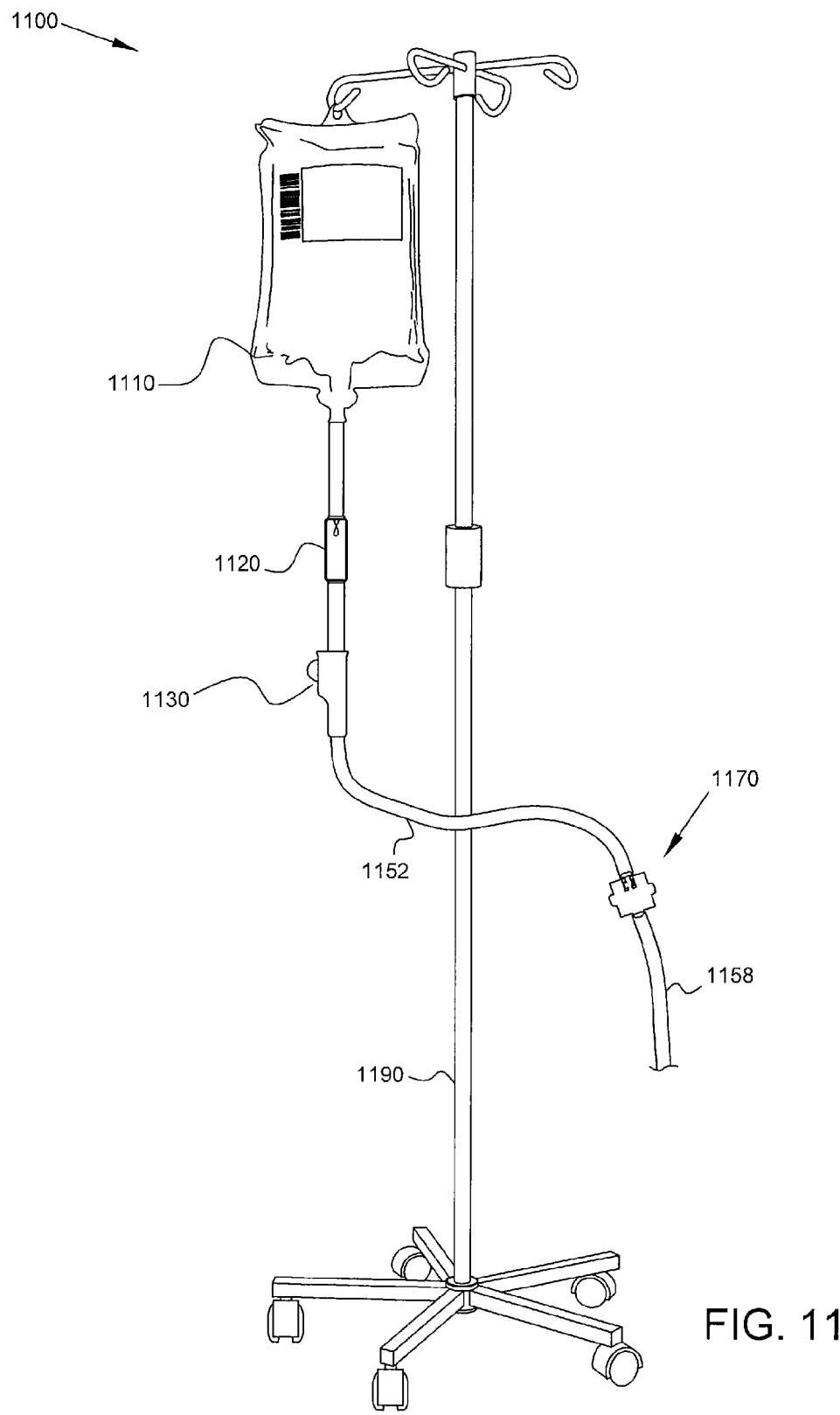
FIG. 11 is a perspective view of an intravenous (IV) fluid administration system according to some embodiments of the present disclosure.

The inventor has observed that utilizing a chamber including a plurality of connector ports, where at least the connector port configured to receive fluid from a gravity-fed IV fluid source is automatically operated, where any suitable number of connector ports may be selected and utilized, and where any suitable IV fluid sources and sinks can be operably coupled to such chamber via such connector ports and via any selected valve connector or selected tubing, his solutions described herein are easily scalable such that numerous different IV fluids can be injected and flushed efficiently, cost-effectively, and accurately. Referring now to FIG. 11, a perspective view of an intravenous (IV) fluid administration system according to some embodiments is provided. As illustrated in FIG. 11, some embodiments include a source of a first IV fluid 1110, a drip chamber 1120, a roller clamp 1130, tubing 1152 downstream of roller clamp 1130 as described above for FIGS. 2 and 10A-10E, a chamber 1170 as described above for FIGS. 10A-10E, and tubing 1158 downstream of chamber 1170 as described above for FIGS. 2 and 10A-10E. As shown in FIG. 11, IV fluid administration system 1100 does not include a stopcock.

Figure 12:
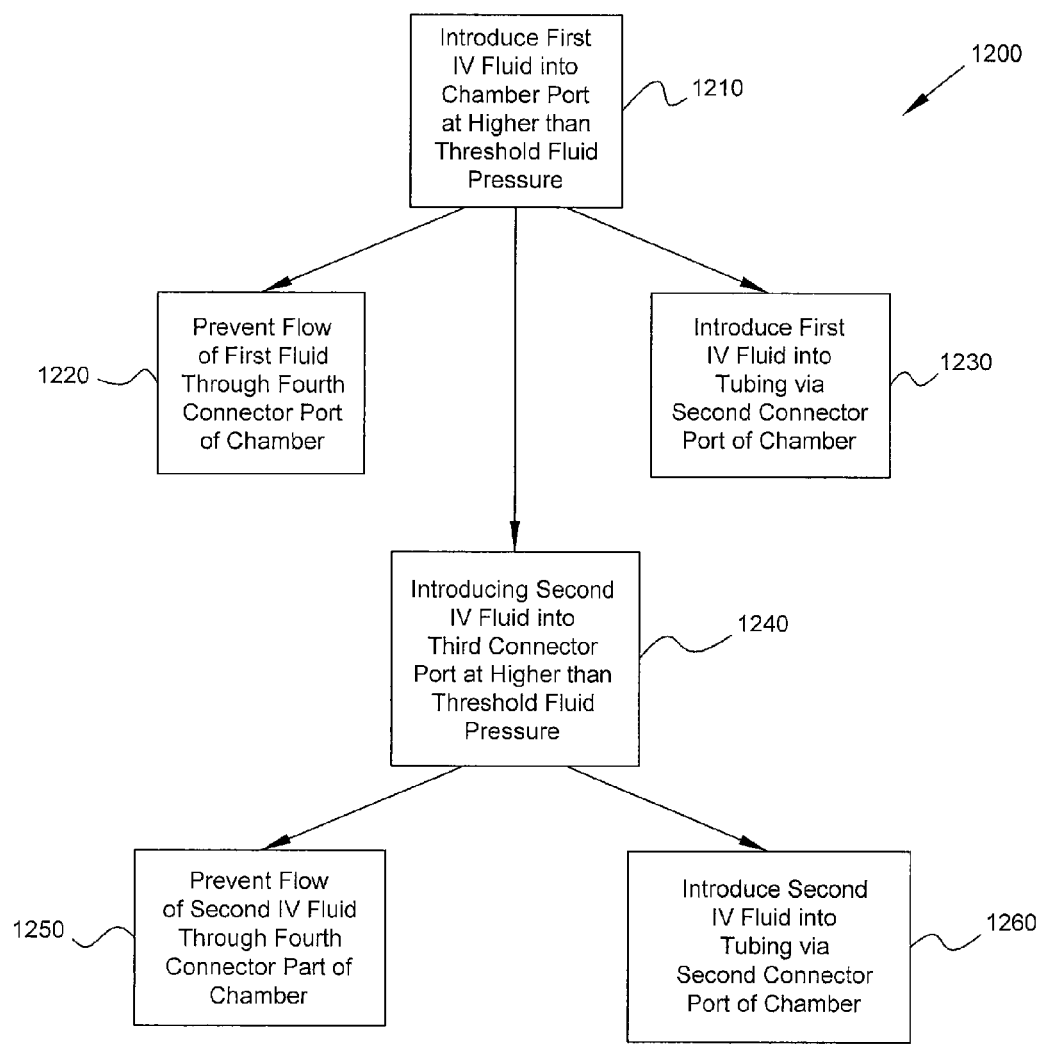
FIG. 12 is a flow chart illustrating a method of flushing a line of an intravenous fluid administration system according to some embodiments.

With reference to FIG. 12, a flow chart illustrating a method 1200 of flushing a line of an intravenous fluid administration system according to some embodiments is provided. At block 1210, a first IV fluid is introduced into a first connector port (e.g. 1072) of a chamber (e.g. 1070) comprising a plurality of connector ports (e.g. 1071, 1072, 1073, 1074) and at a fluid pressure exceeding a threshold pressure of the chamber. In various embodiments, the first IV fluid includes a drug, an antibiotic, or an anesthetic. In various embodiments, the threshold pressure of the chamber is a threshold pressure of a check valve (e.g. 1076) disposed downstream of a fourth connector port (e.g. 1071) of the chamber (e.g. 1070). At block 1220, the introducing step (at block 1210) automatically prevents the flow of the first IV fluid through the fourth connector port (e.g. 1071) of the chamber (e.g. 1070). In various embodiments, the introducing step (at block 1210) automatically shuts the check valve (e.g. 1076) disposed downstream of the fourth connector port (e.g. 1071) of the chamber (e.g. 1070) to prevent the flow of the first IV fluid through the fourth connector port.

At block 1230, the first IV fluid is introduced into tubing (e.g. 1158, FIG. 2 tubing 258, FIG. 8 tubing 858) configured to transport IV fluid for intravenous infusion to a subject (not shown) via a second connector port (e.g. 1073) of the chamber. At block 1240, a second IV fluid is introduced into a third connector port (e.g. 1074) of the chamber (e.g. 1070) at a fluid pressure exceeding a threshold pressure of the chamber. In various embodiments, the second IV fluid is a solution including saline. In various embodiments, the introducing step (at block 1240), includes operating a reservoir pump (e.g. FIG. 2 reservoir pump 260, FIG. 8 reservoir pump 860) upstream of the third connector port (e.g. 1074) of the chamber (e.g. 1070) as described above for FIGS. 2, 3A-4B, 8, and 10A-10E. At block 1250, the introducing step (at block 1240) automatically prevents the flow of the second IV fluid through the fourth connector port (e.g. 1071) of the chamber (e.g. 1070). In various embodiments, the introducing step (at block 1240) automatically shuts the check valve (e.g. 1076) disposed downstream of the fourth connector port (e.g. 1071) of the chamber (e.g. 1070) to prevent the flow of the second IV fluid through the fourth connector port. At block 1250, the second IV fluid is introduced into tubing (e.g. 1158, FIG. 2 tubing 258, FIG. 8 tubing 858) configured to transport IV fluid for intravenous infusion to a subject (not shown) via the second connector port (e.g. 1073) of the chamber.

In various embodiments, the method 1200 includes releasing a reservoir pump (e.g. FIG. 2 reservoir pump 260, FIG. 8 reservoir pump 860), operably coupled to the chamber (e.g. 1070) via the third connector port (e.g. 1074), such that the reservoir pump automatically fills itself with second IV fluid from a source (e.g. FIG. 2 source 210, FIG. 8 source 810) upstream of the reservoir pump, and such that the chamber (e.g. 1070) automatically reconfigures itself to receive a third IV fluid from a fluid source (e.g. FIG. 2 source 210, FIG. 8 source 810) upstream of the chamber (e.g. 1070) and at a fluid pressure less than the threshold pressure of the chamber. In various embodiments, the chamber (e.g. 1070) receives the third IV fluid via the fourth connector port (e.g. 1071). In various embodiments, the third IV fluid is a solution including saline. In various embodiments, each of the introducing step (at block 1240) and the introducing step (at block 1210) automatically prevents the flow of the third IV fluid into the tubing (e.g. 1158, FIG. 2 tubing 258, FIG. 8 tubing 858) configured to transport IV fluid for intravenous infusion to a subject (not shown) via the second connector port (e.g. 1073) of the chamber. In various embodiments, the introducing steps (at blocks 1210 and 1240) each automatically shut the check valve (e.g. 1076) disposed downstream of the fourth connector port (e.g. 1071) of the chamber (e.g. 1070) to prevent the flow of the third IV fluid through the check valve (e.g. 1076).

Figure 13:
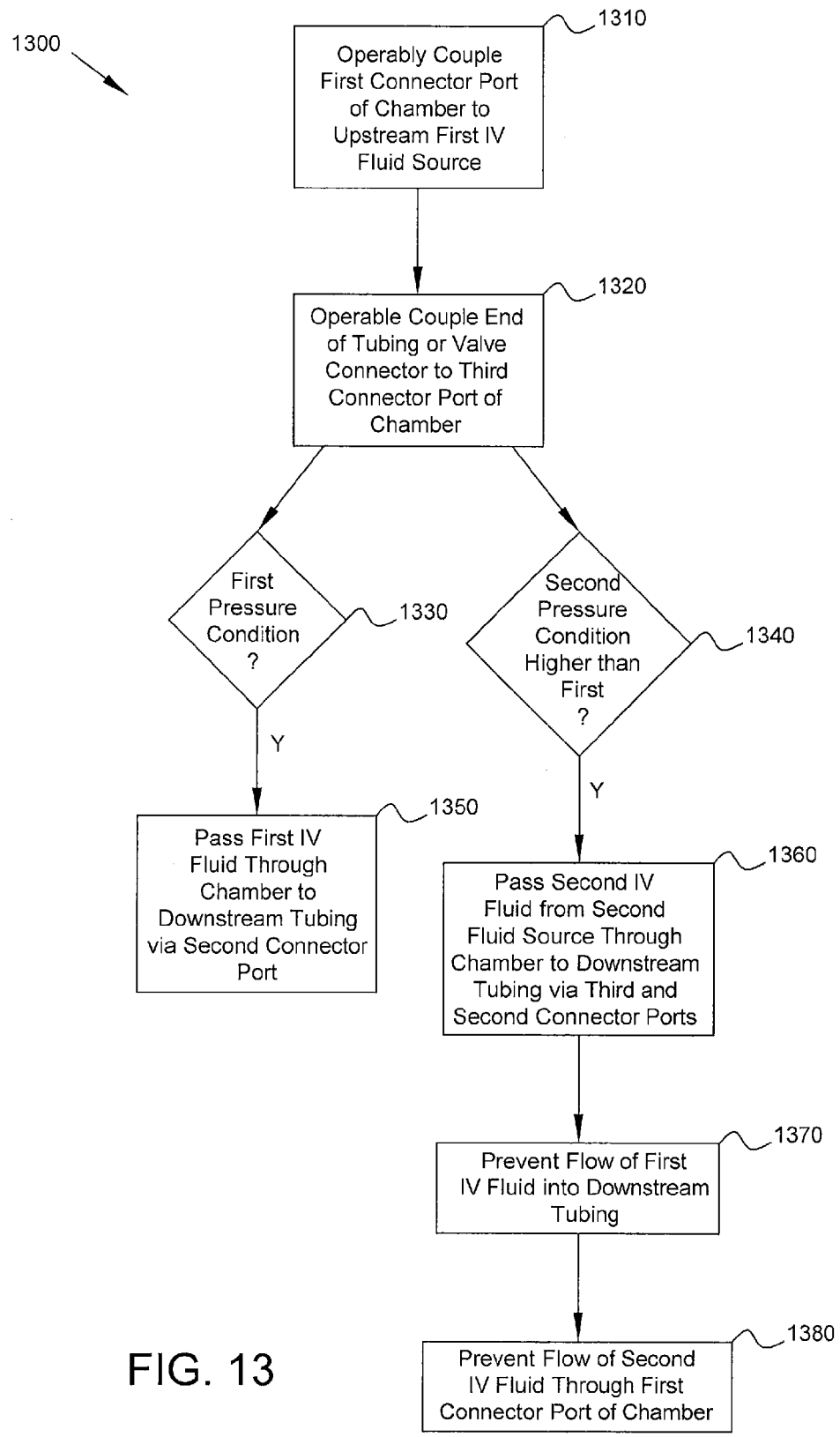
FIG. 13 is a flow chart illustrating a method according to some embodiments of the present disclosure.

Referring now to FIG. 13, a flow chart illustrating a method 1300 according to some embodiments is provided. At block 1310, a first one (e.g. 1071) of a plurality of connector ports (e.g. 1071, 1072, 1073, 1074) of a chamber (e.g. 1070) is operably coupled to an upstream first source of a first IV fluid (e.g. 1110, FIG. 2 source 210, FIG. 8 source 810). At block 1320, a third one (e.g. 1074) of the plurality of connector ports of the chamber (e.g. 1070) is operably coupled to an end of tubing or a valve connector as described above for FIGS. 10A-10E. In various embodiments, the end of tubing or the valve connector is operably coupled to a reservoir pump (e.g. FIG. 2 reservoir pump 260, FIG. 8 reservoir pump 860) configured to automatically refill itself with the second IV fluid from a second upstream IV fluid source (e.g. FIG. 2 source 210, FIG. 6 source 610a or 610b, FIG. 8 source 810) as described above for FIGS. 2, 3A-4B, 6, 8, and 10A-10E. In various embodiments, the first and second IV fluid sources are the same source (e.g. FIG. 2 source 210, FIG. 6 source 610a, FIG. 8 source 810) and the first and second IV fluids are the same type of fluid. In some embodiments, the first and second IV fluid sources are different sources (e.g. FIG. 6 source 610a and source 610b) and the first and second IV fluids are different types of fluid. In some embodiments, the valve connector includes a luer. In some embodiments, the valve connector includes a needle-free valve, an aspiration valve, a trumpet valve, or a normally closed check valve.

At block 1330, during operation, a pressure condition is evaluated as to whether a first pressure condition exists. At block 1350, if a first pressure condition is determined to exist (at block 1330), the first IV fluid is passed through the chamber (e.g. 1070) to tubing downstream (e.g. 1058, 1158, FIG. 2 tubing 258, FIG. 8 tubing 858) of the chamber (e.g. 1070) via the first connector port (e.g. 1071) and a second one (e.g. 1073) of the plurality of connector ports of the chamber (e.g. 1070). At block 1340, during operation, a pressure condition is evaluated as to whether a second pressure condition higher than the first pressure condition exists. At block 1360, if a second pressure condition higher than the first pressure condition is determined to exist (at block 1340), the second IV fluid is passed through the chamber (e.g. 1070) to tubing downstream (e.g. 1058, 1158, FIG. 2 tubing 258, FIG. 8 tubing 858) of the chamber (e.g. 1070) via the third (e.g. 1074) and second (e.g. 1073) connector ports of the chamber (e.g. 1070). At block 1360, if the second pressure condition is determined to exist (at block 1340), the first IV fluid is prevented from flowing into the tubing downstream (e.g. 1058, 1158, FIG. 2 tubing 258, FIG. 8 tubing 858) of the chamber (e.g. 1070). At block 1370, if the second pressure condition is determined to exist (at block 1340), the second IV fluid is prevented from flowing through the first connector port (e.g. 1071) of the chamber (e.g. 1070).

In some embodiments, various steps of the method can be implemented (e.g., introducing IV fluids) by a general purpose computer programmed in accordance with the principals discussed herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous.

While various embodiments are described herein, it is to be understood that the embodiments described are illustrative only and that the scope of the subject matter is to be accorded a full range of equivalents, many variations and modifications naturally occurring to those of skill in the art from a perusal hereof.

What I claim is:

1. An apparatus for dispensing fluid intravenously to a subject, comprising:
    an enclosed chamber comprising a plurality of connector ports, the chamber configured to:
        operate in fluid communication with an upstream first source of a first fluid via a first one of the plurality of connector ports of the chamber; and
        during operation, pass therethrough to tubing downstream of the chamber, under a first pressure condition, the first fluid from the upstream first fluid source via a second one of the plurality of connector ports of the chamber; and
        wherein a third one of the plurality of connector ports of the chamber is configured to connect to an end of tubing or a valve connector such that, during operation, the chamber is configured to, under a second pressure condition higher than the first pressure condition:
            pass therethrough to the tubing downstream of the chamber a second fluid from a second fluid source via the third and second connector ports of the chamber;
            prevent flow of the first fluid into the tubing downstream of the chamber; and
            prevent flow of the second fluid through the first connector port of the chamber.

2. The apparatus of claim 1, wherein a fourth one of the plurality of connector ports of the chamber is configured to connect to an end of tubing or a valve connector such that, during operation, the chamber is configured to, under a third pressure condition higher than the first pressure condition:
    pass therethrough to the tubing downstream of the chamber a third fluid from a third fluid source via the fourth and second connector ports of the chamber;
    prevent flow of the first fluid into the tubing downstream of the chamber; and
    prevent flow of the third fluid through the first connector port of the chamber.

3. The apparatus of claim 1, wherein the end of tubing or the valve connector is operably coupled to a reservoir configured to automatically refill itself with the second fluid from a second upstream fluid source.

4. The apparatus of claim 3, wherein the valve connector comprises a normally closed check valve.

5. The apparatus of claim 1, wherein the valve connector comprises a luer.

6. The apparatus of claim 5, wherein the second fluid source is a syringe.

7. The apparatus of claim 1, wherein the valve connector comprises a needle-free valve, an aspiration valve, a trumpet valve, or a normally closed check valve.

8. The apparatus of claim 1, wherein the first and second fluid sources are the same source and the first and second fluids are the same type of fluid.

9. A method of flushing a line of an intravenous fluid administration system, comprising:
    introducing a first fluid into tubing configured to transport fluid for intravenous infusion to a subject via a first connector port and a second connector port of a chamber comprising a plurality of connector ports and at a fluid pressure exceeding a threshold pressure of the chamber; and
    introducing a second fluid into the tubing via a third connector port and the second connector port of the chamber and at a fluid pressure exceeding the threshold pressure of the chamber;

wherein each of the introducing steps automatically prevents the flow of the first fluid or the second fluid through a fourth connector port of the chamber.

10. The method of claim 9, wherein the first fluid comprises a drug or an antibiotic and the chamber is enclosed.

11. The method of claim 10, wherein the second fluid is a solution comprising saline.

12. The method of claim 9, wherein the introducing the second fluid step further comprises operating a reservoir upstream of the third connector port of the chamber.

13. The method of claim 12, further comprising:
releasing the reservoir such that the reservoir automatically fills itself with second fluid from a source upstream of the reservoir and such that the chamber automatically reconfigures itself to receive a third fluid from a fluid source upstream of the chamber and at a fluid pressure less than the threshold pressure.

14. The method of claim 13, wherein each of the introducing steps automatically shuts off the flow of the third fluid into the tubing.

15. A method comprising:
operably coupling a first one of a plurality of connector ports of a chamber to an upstream first source of a first fluid such that the chamber is configured to, during operation, pass therethrough to tubing downstream of the chamber, under a first pressure condition, the first fluid via a second one of the plurality of connector ports of the chamber; and
operably coupling an end of tubing or a valve connector to a third one of the plurality of connector ports of the chamber such that, during operation, the chamber is configured to, under a second pressure condition higher than the first pressure condition, automatically:
pass therethrough to the tubing downstream of the chamber a second fluid from a second fluid source via the third and second connector ports;
shut off flow of the first fluid into the tubing downstream of the chamber; and
prevent flow of the second fluid through the first connector port.

16. The method of claim 15, further comprising:
operably coupling an end of tubing or a valve connector to a fourth one of the plurality of connector ports of the chamber such that, during operation, the chamber is configured to, under a third pressure condition higher than the first pressure condition, automatically:
pass therethrough to the tubing downstream of the chamber a third fluid from a third fluid source via the fourth and second connector ports;
shut off flow of the first fluid into the tubing downstream of the chamber; and
prevent flow of the third fluid through the first connector port.

17. The method of claim 15, further comprising:
operably coupling the end of tubing or the valve connector to a reservoir configured to automatically refill itself with the second fluid from a second upstream fluid source.

18. The method of claim 15, wherein the chamber is enclosed.

19. The method of claim 15, wherein the valve connector comprises a luer, a needle-free valve, an aspiration valve, a trumpet valve, or a normally closed check valve.

20. The method of claim 15, wherein the first and second fluid sources are the same source and the first and second fluids are the same type of fluid.

* * * * *